(12) United States Patent
Suzuki et al.

(10) Patent No.: US 9,911,923 B2
(45) Date of Patent: Mar. 6, 2018

(54) LIGHT-EMITTING ELEMENT, LIGHT-EMITTING DEVICE, ELECTRONIC DEVICE, LIGHTING DEVICE, AND PYRENE-BASED COMPOUND

(71) Applicant: Semiconductor Energy Laboratory Co., Ltd., Kanagawa-ken (JP)

(72) Inventors: Hiroki Suzuki, Kanagawa (JP); Satoshi Seo, Kanagawa (JP); Sachiko Kawakami, Kanagawa (JP); Tsunenori Suzuki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 15/152,091

(22) Filed: May 11, 2016

(65) Prior Publication Data

US 2016/0254451 A1    Sep. 1, 2016

Related U.S. Application Data

(63) Continuation of application No. 13/644,275, filed on Oct. 4, 2012, now Pat. No. 9,343,681.

(30) Foreign Application Priority Data

Oct. 11, 2011 (JP) ................................ 2011-223634

(51) Int. Cl.
*H01L 51/50* (2006.01)
*H01L 51/00* (2006.01)
(Continued)

(52) U.S. Cl.
CPC .......... *H01L 51/006* (2013.01); *C07D 209/88* (2013.01); *C09K 11/025* (2013.01);
(Continued)

(58) Field of Classification Search
None
See application file for complete search history.

(56) References Cited

U.S. PATENT DOCUMENTS 6,905,788 B2   6/2005   Tyan et al.
7,709,104 B2   5/2010   Saitoh et al.
(Continued)

FOREIGN PATENT DOCUMENTS

EP   2 330 652 A2   6/2011
EP   2 372 803 A1   10/2011
(Continued)

OTHER PUBLICATIONS

Shih, P. et al., "A Novel Fluorene-Triphenylamine Hybrid That Is a Highly Efficient Host Material For Blue-,Green-, and Red-Light-Emitting Electrophosphorescent Devices," Advanced Functional Materials, 2007, vol. 17, pp. 3514-3520.
(Continued)

*Primary Examiner* — Gregory D Clark
(74) *Attorney, Agent, or Firm* — Husch Blackwell LLP

(57) ABSTRACT

A highly efficient light-emitting element capable of providing a plurality of emission colors is provided, which does not easily deteriorate and can minimize a decrease in external quantum efficiency even when a light-emitting layer has a stacked structure. A light-emitting device, an electronic device, and a lighting device which have low power consumption and long lifetime are provided. A light-emitting element includes a plurality of light-emitting layers stacked between a pair of electrodes. The light-emitting layers each contain a host material and a guest material. The guest materials of the light-emitting layers are substances which have different HOMO levels but have substantially the same LUMO levels and emit light of different colors. A light-
(Continued)

emitting device, an electronic device, and a lighting device are fabricated using the light-emitting element.

14 Claims, 18 Drawing Sheets

(51) Int. Cl.
  *C07D 209/88*    (2006.01)
  *C09K 11/02*    (2006.01)
  *C09K 11/06*    (2006.01)
  *H01L 51/52*    (2006.01)

(52) U.S. Cl.
  CPC .......... *C09K 11/06* (2013.01); *H01L 51/0052* (2013.01); *H01L 51/0054* (2013.01); *H01L 51/0059* (2013.01); *H01L 51/0061* (2013.01); *H01L 51/0072* (2013.01); *H01L 51/504* (2013.01); *H01L 51/5036* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *H01L 51/5004* (2013.01); *H01L 51/5278* (2013.01); *H01L 2251/552* (2013.01); *Y02B 20/181* (2013.01)

(56) References Cited

U.S. PATENT DOCUMENTS

| | | |
|---|---|---|
| 8,486,543 B2 | 7/2013 | Seo et al. |
| 8,541,113 B2 | 9/2013 | Je et al. |
| 8,940,412 B2 | 1/2015 | Takashima et al. |
| 2004/0110958 A1 | 6/2004 | Nishiyama et al. |
| 2005/0221124 A1 | 10/2005 | Hwang et al. |
| 2006/0180812 A1 | 8/2006 | Sakata et al. |
| 2007/0215867 A1 | 9/2007 | Kawakami et al. |
| 2007/0215889 A1 | 9/2007 | Kawakami et al. |
| 2008/0122345 A1 | 5/2008 | Sakata et al. |
| 2008/0124572 A1 | 5/2008 | Mizuki et al. |
| 2008/0206598 A1 | 8/2008 | Ohsawa et al. |
| 2008/0213624 A1 | 9/2008 | Lecloux et al. |
| 2010/0052526 A1 | 3/2010 | Je et al. |
| 2011/0095678 A1 | 4/2011 | Ogita et al. |
| 2011/0248246 A1 | 10/2011 | Ogita et al. |
| 2013/0299798 A1 | 11/2013 | Seo et al. |

FOREIGN PATENT DOCUMENTS

| | | |
|---|---|---|
| EP | 2 713 415 A1 | 4/2014 |
| JP | 2006-176493 A | 7/2006 |
| JP | 2006-269232 A | 10/2006 |
| JP | 2007-015933 A | 1/2007 |
| JP | 2010-053131 A | 3/2010 |
| JP | 2011-139044 A | 7/2011 |
| KR | 2011-0041725 A | 4/2011 |
| KR | 2011-0041728 A | 4/2011 |
| KR | 2011-0081698 A | 7/2011 |
| WO | WO 2010/074087 A1 | 7/2010 |

OTHER PUBLICATIONS

Wee, K. et al., "Emission Color Tuning and Deep Blue Dopant Materials Based on 1,6-Bis(N-phenyl-p-(R)-phenylamino)pyrene," Journal of Organic Chemistry, Aug. 19, 2009, vol. 74, No. 21, pp. 8472-8475.

LIGHT-EMITTING ELEMENT, LIGHT-EMITTING DEVICE, ELECTRONIC DEVICE, LIGHTING DEVICE, AND PYRENE-BASED COMPOUND

This application is a continuation of copending U.S. application Ser. No. 13/644,275, filed on Oct. 4, 2012 which is incorporated herein by reference.

BACKGROUND OF THE INVENTION

1. Field of the Invention

One embodiment of the present invention relates to light-emitting elements having a plurality of emission colors. One embodiment of the present invention also relates to light-emitting devices, electronic devices, and lighting devices. One embodiment of the present invention further relates to novel pyrene-based compounds.

2. Description of the Related Art

In recent years, research and development have been extensively conducted on light-emitting elements using electroluminescence (EL). In a basic structure of such a light-emitting element, a layer containing a light-emitting substance is interposed between a pair of electrodes. By applying voltage to this element, light emission from the light-emitting substance can be obtained.

Since such a light-emitting element is of self-light-emitting type, it is considered that the light-emitting element has advantages over a liquid crystal display in that visibility of pixels is high, backlight is not required, and so on and is therefore suitable as flat panel display elements. In addition, it is also a great advantage that the light-emitting element can be manufactured as a thin and lightweight element. Furthermore, very high speed response is also one of the features of such elements.

Furthermore, since such light-emitting elements can be formed in the form of a film, they make it possible to provide planar light emission easily. Therefore, large-area elements using planar light emission can be easily formed. This feature is difficult to obtain with point light sources typified by incandescent lamps and LEDs or linear light sources typified by fluorescent lamps. Thus, light-emitting elements also have great potential as planar light sources which can be applied to lighting devices and the like.

Light-emitting elements utilizing electroluminescence are broadly classified according to whether they include an organic compound or an inorganic compound as a light-emitting substance. In the case where an organic compound is used as a light-emitting substance, application of voltage to a light-emitting element causes electrons and holes to be injected into a layer containing the light-emitting organic compound from a pair of electrodes, whereby current flows. The carriers (electrons and holes) are recombined, and thus the light-emitting organic compound is excited. The light-emitting organic compound returns to a ground state from the excited state, thereby emitting light. Note that the excited state of an organic compound can be a singlet excited state and a triplet excited state, and light emission from the singlet excited state (S*) is referred to as fluorescence, and light emission from the triplet excited state (T*) is referred to as phosphorescence.

A function as a light-emitting layer of a light-emitting element formed using a light-emitting organic compound can be achieved with the light-emitting organic compound alone. However, a method for forming a light-emitting layer in which a light-emitting organic compound is dispersed in a matrix of another substance is also employed for the purpose of preventing concentration quenching of the light-emitting organic compound, for example. Note that a substance serving as a matrix is called a host material, and a substance dispersed in the matrix is called a guest material.

In that case, carriers (electrons and holes) injected from both electrodes are recombined in the host material of the light-emitting layer, and the guest material receives the energy and emits light. Therefore, it is known that light emission with high luminance and high color purity can be achieved.

In addition, light-emitting elements which emit white light have recently been employed for lighting purposes. In such a case, white light emission can be achieved with the use of a plurality of light-emitting materials. However, a light-emitting layer containing plural kinds of light-emitting materials causes problems such as a change in chromaticity and a decrease in external quantum efficiency, due to energy transfer between the light-emitting materials.

Against these problems, it has been proposed to stack a plurality of light-emitting layers, each containing a different light-emitting material (see, for example, Reference 1). However, in that case, a problem is a high possibility of deterioration because of charge accumulation at the interface between the stacked layers, for example.

REFERENCE

[Reference 1] Japanese Published Patent Application No. 2006-269232

SUMMARY OF THE INVENTION

One embodiment of the present invention provides a highly efficient light-emitting element capable of providing a plurality of emission colors, which does not easily deteriorate and can minimize a decrease in external quantum efficiency even when a light-emitting layer has a stacked structure. One embodiment of the present invention also provides a novel pyrene-based compound suitable for the light-emitting layer of the above light-emitting element. One embodiment of the present invention also provides a highly efficient light-emitting element by using the novel pyrene-based compound. One embodiment of the present invention also provides a light-emitting device, an electronic device, and a lighting device which have low power consumption and long lifetime, by using the light-emitting element containing the novel pyrene-based compound.

One embodiment of the present invention is a light-emitting element including a plurality of light-emitting layers stacked between a pair of electrodes. The light-emitting layers each contain a host material and a guest material. The guest materials of the light-emitting layers are substances which have different HOMO levels but have substantially the same LUMO levels and emit light of different colors. Note that LUMO levels within a range of ±0.2 eV, preferably within a range of ±0.1 eV, are regarded as substantially the same LUMO levels.

Note that different guest materials are used for the plurality of light-emitting layers, and as the different guest materials, materials having different HOMO levels but having substantially the same LUMO levels are used. Accordingly, a stack-type light-emitting layer can be formed which has a hole-trapping property at the interface between the stacked light-emitting layers but is unlikely to block electron transfer. Therefore, a light-emitting element having high emission efficiency and long lifetime can be formed.

In the above light-emitting element, the host materials of the light-emitting layers are preferably a common (in other words, the same) material, which is preferably a bipolar material. The use of the common bipolar material as the host materials can reduce the influence of the host materials on the carrier-transport property even in the light-emitting layer having a stacked structure and can facilitate element design.

The common host material used for the light-emitting layers preferably contains condensed aromatic hydrocarbon in addition to being bipolar. This is because a material containing condensed aromatic hydrocarbon has a higher molecular weight and better thermophysical properties. With the use of the material containing condensed aromatic hydrocarbon, a light-emitting element having high heat resistance can be formed. Note that examples of the material containing condensed aromatic hydrocarbon include materials containing anthracene, triphenylene, pyrene, phenanthrene, or fluoranthene.

In the above light-emitting element, the guest materials used for the light-emitting layers are preferably pyrene-based compounds having different structures. The pyrene-based compounds are preferably pyrenediamine compounds, particularly, pyrene-1,6-diamine compounds. In addition, the host material is preferably a material containing anthracene, particularly, a material containing anthracene and having no amine skeleton.

Another embodiment of the present invention is a novel pyrene-based compound which can be used as a guest material in each light-emitting layer of the above light-emitting element and is represented by the following general formula (G1).

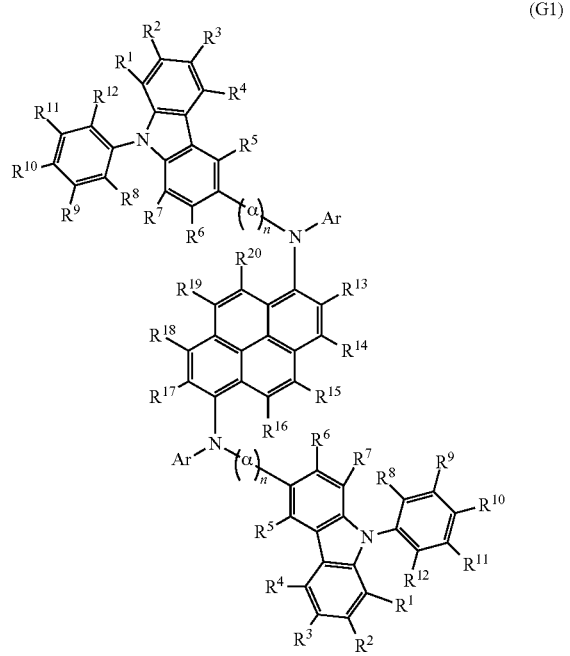

(G1)

In the formula, Ar represents a substituted or unsubstituted aryl group having 6 to 10 carbon atoms, α represents a substituted or unsubstituted phenylene group, and $R^1$ to $R^{12}$ separately represent a hydrogen atom or an alkyl group having 1 to 4 carbon atoms. Further, $R^{13}$ to $R^{20}$ separately represent a hydrogen atom or an alkyl group having 1 to 6 carbon atoms. Further, n is 0 or 1.

Another embodiment of the present invention is a novel pyrene-based compound represented by the following general formula (G2).

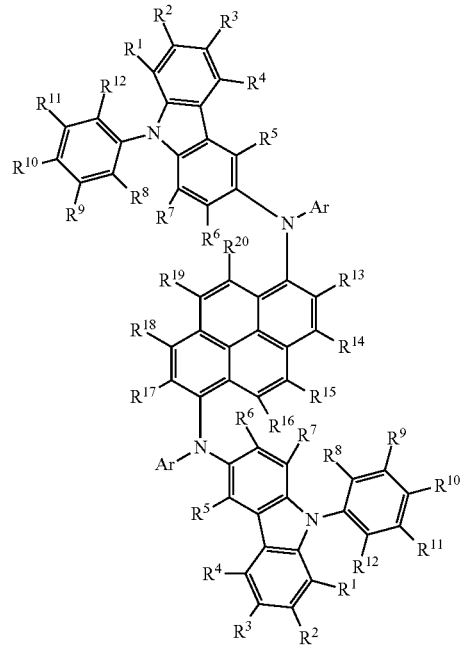

(G2)

In the formula, Ar represents a substituted or unsubstituted aryl group having 6 to 10 carbon atoms, and $R^1$ to $R^{12}$ separately represent a hydrogen atom or an alkyl group having 1 to 4 carbon atoms. Further, $R^{13}$ to $R^{20}$ separately represent a hydrogen atom or an alkyl group having 1 to 6 carbon atoms.

Another embodiment of the present invention is a novel pyrene-based compound represented by the following general formula (G3).

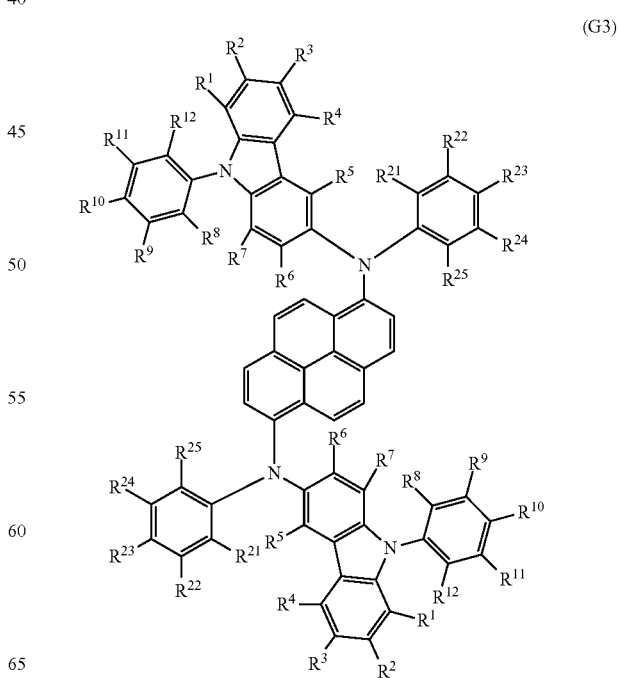

(G3)

In the formula, $R^1$ to $R^{12}$ and $R^{21}$ to $R^{25}$ separately represent a hydrogen atom or an alkyl group having 1 to 4 carbon atoms.

Another embodiment of the present invention is a novel pyrene-based compound represented by the following structural formula (100).

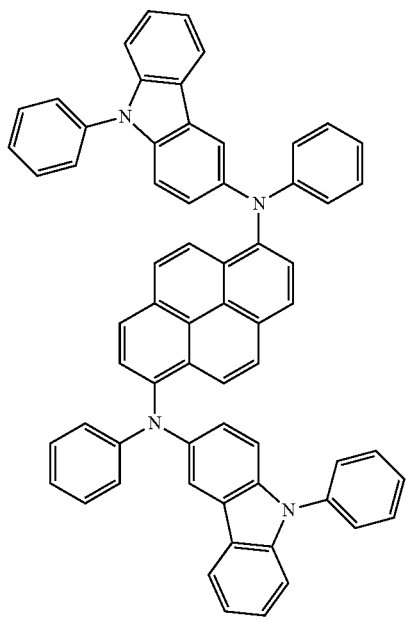

(100)

The novel pyrene-based compounds which are embodiments of the present invention emit light of a blue-green color with high color purity. Therefore, a light-emitting element including a plurality of light-emitting layers stacked between a pair of electrodes, in which the light-emitting layers each contain a host material and a guest material and plural kinds of pyrene-based compounds are used as the guest materials of the light-emitting layers, can provide light of emission colors of all the guest materials at the same time, when the light-emitting layers are formed by using as a guest material at least one of above-described novel pyrene-based compounds which are embodiments of the present invention and by using as another guest material another pyrene-based compound having a different HOMO level but having substantially the same LUMO level.

When a light-emitting layer containing an orange light-emitting substance is further stacked over the light-emitting layer having a stacked structure containing different guest materials in the light-emitting element of one embodiment of the present invention, the light-emitting element can emit excellent white light.

Further, the present invention includes, in its scope, electronic devices and lighting devices including light-emitting devices as well as light-emitting devices including light-emitting elements. The light-emitting device in this specification refers to an image display device, a light-emitting device, and a light source (e.g., a lighting device). In addition, the light-emitting device includes all the following modules: a module in which a connector, such as a flexible printed circuit (FPC), a tape automated bonding (TAB) tape, or a tape carrier package (TCP), is attached to a light-emitting device; a module in which a printed wiring board is provided at the end of a TAB tape or a TCP; and a module in which an integrated circuit (IC) is directly mounted on a light-emitting device by a chip-on-glass (COG) method.

One embodiment of the present invention can provide a highly efficient light-emitting element capable of providing a plurality of emission colors, which does not easily deteriorate and can minimize a decrease in external quantum efficiency even when a light-emitting layer has a stacked structure. One embodiment of the present invention can also provide a novel pyrene-based compound suitable for the light-emitting layer of the above light-emitting element. One embodiment of the present invention can also provide a highly efficient light-emitting element by using the novel pyrene-based compound. One embodiment of the present invention can also provide a light-emitting device, an electronic device, and a lighting device which have low power consumption and long lifetime, by using the light-emitting element containing the novel pyrene-based compound.

DETAILED DESCRIPTION OF THE INVENTION

Embodiments of the present invention will be described below with reference to the drawings. Note that the present invention is not limited to the following description, and various changes and modifications can be made without departing from the spirit and scope of the invention. Therefore, the present invention should not be construed as being limited to the description in the following embodiments.

Embodiment 1

In this embodiment, a light-emitting element which is one embodiment of the present invention will be described with reference to FIGS. 1A and 1B.

Figure 1A:
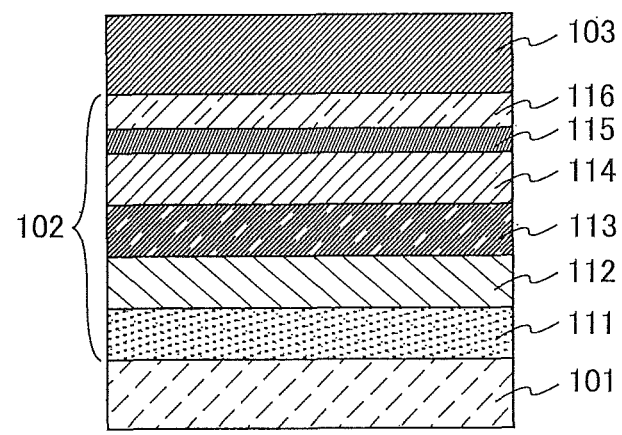
FIGS. 1A and 1B illustrate a structure of a light-emitting element.
Figure 1B:
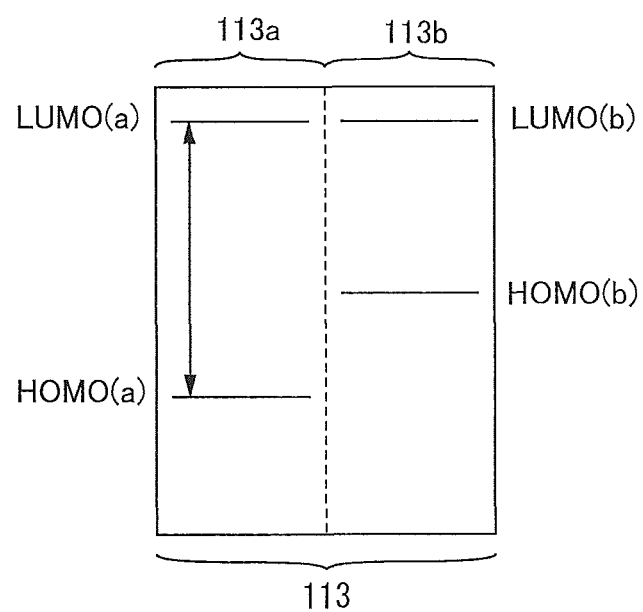

In the light-emitting element described in this embodiment, as illustrated in FIG. 1A, an EL including a light-emitting layer 113 is provided between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, a charge generation layer (E) 116, and the like in addition to the light-emitting layer 113.

Application of a voltage to such a light-emitting element causes holes injected from the first electrode 101 side and electrons injected from the second electrode 103 side to recombine in the light-emitting layer 113 and a substance contained in the light-emitting layer 113 to be raised to an excited state. Then, light is emitted when the substance in the excited state returns to the ground state.

Note that the light-emitting layer 113 in the EL layer 102 has a stacked structure including a plurality of layers. For example, when having a stacked structure of two layers, the light-emitting layer 113 includes a first light-emitting layer 113a and a second light-emitting layer 113b as illustrated in FIG. 1B.

The first light-emitting layer 113a and the second light-emitting layer 113b are formed so as to have substantially the same LUMO levels (LUMO(a)≈LUMO(b)) but have different HOMO levels (HOMO(a)≠HOMO(b)). In the case where the HOMO level of the first light-emitting layer 113a (HOMO(a)) is deeper than the HOMO level of the second light-emitting layer 113b (HOMO(b)) as illustrated in FIG. 1B, a hole-trapping property is accordingly acquired, and thus a recombination region for holes and electrons can be confined within the light-emitting layer. Therefore, the light-emitting element can have higher emission efficiency than a conventional light-emitting element. Thus, a guest material contained in the anode side of the light-emitting layer (the first light-emitting layer) preferably emits light of a shorter wavelength than that of a guest material contained in the cathode side (the second light-emitting layer).

In the case where the first light-emitting layer 113a and the second light-emitting layer 113b are formed so as to have substantially the same LUMO levels (LUMO(a)≈LUMO(b)) but have different HOMO levels (HOMO(a)≠HOMO(b)), the first light-emitting layer 113a and the second light-emitting layer 113b are formed using the same host material and different guest materials. Note that even when the light-emitting layers (the first light-emitting layer 113a and the second light-emitting layer 113b) emit light of different colors, holes are trapped at the interface between the first light-emitting layer 113a and the second light-emitting layer 113b because the different guest materials are used, and thus light of different colors can be emitted at the same time. This is a great advantage in, for example, obtaining white light in combination with another light-emitting layer because color rendering properties can be improved.

The hole-injection layer 111 in the EL layer 102 is a layer containing a substance having a high hole-transport property and an acceptor substance. When electrons are extracted from the substance having a high hole-transport property owing to the acceptor substance, holes are generated. Thus, holes are injected from the hole-injection layer 111 into the light-emitting layer 113 through the hole-transport layer 112.

The charge generation layer (E) 116 is a layer containing a substance having a high hole-transport property and an acceptor substance. Electrons are extracted from the substance having a high hole-transport property owing to the acceptor substance, and the extracted electrons are injected from the electron-injection layer 115 having an electron-injection property into the light-emitting layer 113 through the electron-transport layer 114.

A specific example in which the light-emitting element described in this embodiment is manufactured is described below.

As the first electrode (anode) 101 and the second electrode (cathode) 103, a metal, an alloy, an electrically conductive compound, a mixture thereof, or the like can be used. Specifically, indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), or titanium (Ti) can be used. In addition, an element belonging to Group 1 or Group 2 of the periodic table, for example, an alkali metal such as lithium (Li) or cesium (Cs), an alkaline earth metal such as magnesium (Mg), calcium (Ca), or strontium (Sr), an alloy containing such an element (e.g., MgAg or AlLi), a rare earth metal such as europium (Eu) or ytterbium (Yb), an alloy containing such an element, graphene, or the like can be used. The first electrode (anode) 101 and the second electrode (cathode) 103 can be formed by, for example, a sputtering method, an evaporation method (including a vacuum evaporation method), or the like.

Examples of the substance having a high hole-transport property which is used for the hole-injection layer 111, the hole-transport layer 112, and the charge generation layer (E) 116 include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris (N,N'-diphenylamino)triphenylamine (abbreviation: TDATA), 4,4',4''-tris[N-(3-methylphenyl)-N-phenylamino] triphenylamine (abbreviation: MTDATA), and 4,4'-bis[N-(spiro-9,9'-bifluoren-2-yl)-N-phenylamino]biphenyl (abbreviation: BSPB), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1). Other examples include carbazole derivatives such as 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances mentioned here are mainly substances that have a hole mobility of $10^{-6}$ cm$^2$/Vs or more. Note that other than these substances, any substance that has a property of transporting more holes than electrons may be used.

Still other examples include high molecular compounds such as poly(N-vinylcarbazole) (abbreviation: PVK), poly (4-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), and poly[N,N'-bis(4-butylphenyl)-N,N'-bis (phenyl)benzidine](abbreviation: Poly-TPD).

Further, examples of the acceptor substance that is used for the hole-injection layer 111 and the charge generation layer (E) 116 include oxides of transition metals, oxides of metals belonging to Groups 4 to 8 of the periodic table, and the like. Specifically, molybdenum oxide is particularly preferable. Alternatively, an organic compound may be used as the acceptor substance.

The light-emitting layer 113 has a stacked structure, and the light-emitting layers each contain a host material and a guest material. Note that the host materials of the light-emitting layers are preferably a common (in other words, the same) material having a higher triplet excitation energy than the guest materials, which is preferably a bipolar material. The material further preferably contains condensed aromatic hydrocarbon in addition to being bipolar. Specific examples include materials containing anthracene, triphenylene, pyrene, phenanthrene, or fluoranthene.

The guest materials of the light-emitting layers are substances which have different HOMO levels but have substantially the same LUMO levels and emit light of different colors. The guest materials used for the light-emitting layers are preferably pyrene-based compounds having different structures. The pyrene-based compounds are preferably pyrenediamine compounds, particularly, pyrene-1,6-diamine compounds. This is because a change of the amine skeleton in the pyrenediamine compound can make a change to the emission color and the HOMO level while the LUMO level originating from pyrene is kept substantially the same. Furthermore, the host material is preferably a material containing anthracene, particularly, a material containing anthracene and having no amine skeleton. Such a material has substantially the same LUMO level as the pyrenediamine compound, which allows smooth electron transfer. In addition, it has a deeper HOMO level than the pyrenediamine compound; therefore, hole trapping works effectively. With such a structure, an element having low drive voltage and high emission efficiency can be manufactured. Furthermore, holes are unlikely to pass through the light-emitting layer; therefore, the luminance is unlikely to decrease at the time of constant-current driving even when the electron-transport property or the electron-injection property of the electron-transport layer or the cathode decreases over time. Thus, a light-emitting element having long lifetime can be obtained.

Note that embodiments of pyrene-based compounds which can be used as the guest materials will be described later in Embodiment 2 and Examples 1 to 3. Note that in the light-emitting layer having a stacked structure in the light-emitting element of this embodiment, different materials are used as guest materials of the light-emitting layers, and at least one of the pyrene-based compounds described in Embodiment 2 is used.

The electron-transport layer 114 is a layer that contains a substance having a high electron-transport property. For the electron-transport layer 114, it is possible to use a metal complex such as $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, $Zn(BOX)_2$, or bis[2-(2-hydroxyphenyl)benzothiazolato]zinc (abbreviation: $Zn(BTZ)_2$). Alternatively, it is possible to use a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs). Further alternatively, it is possible to use a high molecular compound such as poly(2,5-pyridine-diyl) (abbreviation: PPy), poly[(9,9-dihexylfluorene-2,7-diyl)-co-(pyridine-3,5-diyl)](abbreviation: PF-Py), or poly[(9,9-dioctylfluorene-2,7-diyl)-co-(2,2'-bipyridine-6,6'-diyl)] (abbreviation: PF-BPy). The substances mentioned here are mainly substances that have an electron mobility of $10^{-6}$ $cm^2/Vs$ or more. Note that other than these substances, any substance that has a property of transporting more electrons than holes may be used for the electron-transport layer.

The electron-transport layer is not limited to a single layer, and may be a stack of two or more layers containing any of the above substances.

The electron-injection layer 115 is a layer that contains a substance having a high electron-injection property. Examples of the substance that can be used for the electron-injection layer 115 include alkali metals, alkaline earth metals, and compounds thereof, such as lithium fluoride (LiF), cesium fluoride (CsF), calcium fluoride ($CaF_2$), and lithium oxide ($LiO_x$), and rare earth metal compounds, such as erbium fluoride ($ErF_3$). Alternatively, the above-mentioned substances for forming the electron-transport layer 114 can be used.

Alternatively, a composite material in which an organic compound and an electron donor (a donor) are mixed may be used for the electron-injection layer 115. Such a composite material, in which electrons are generated in the organic compound by the electron donor, has high electron-injection and electron-transport properties. The organic compound here is preferably a material excellent in transporting the generated electrons, and specifically any of the above substances (such as metal complexes and heteroaromatic compounds) for the electron-transport layer 114 can be used. As the electron donor, a substance showing an electron-donating property with respect to the organic compound may be used. Specifically, alkali metals, alkaline earth metals, and rare earth metals are preferable, and examples include lithium, cesium, magnesium, calcium, erbium, and ytterbium. Any of alkali metal oxides and alkaline earth metal oxides is preferable, examples of which are lithium oxide, calcium oxide, barium oxide, and the like, and a Lewis base such as magnesium oxide or an organic compound such as tetrathiafulvalene (abbreviation: TTF) can be used.

Note that the hole-injection layer 111, the hole-transport layer 112, the light-emitting layer 113, the electron-transport layer 114, the electron-injection layer 115, and the charge generation layer (E) 116 which are mentioned above can each be formed by a method such as an evaporation method (including a vacuum evaporation method), an inkjet method, or a coating method. In the case where the light-emitting layer 113 has a stacked structure, a layer formed by an evaporation method and a layer formed by an inkjet method may be combined.

In the above-described light-emitting element, a current flows due to a potential difference generated between the first electrode 101 and the second electrode 103, and holes and electrons recombine in the EL layer 102, so that light is emitted. Then, this light emission is extracted to the outside through either the first electrode 101 or the second electrode 103 or both. Therefore, either the first electrode 101 or the second electrode 103, or both, is an electrode having a light-transmitting property.

Note that the light-emitting element described in this embodiment is one embodiment of the present invention and is an example of a light-emitting element which includes a light-emitting layer having substantially the same LUMO levels in spite of having different HOMO levels. In such a light-emitting element, a recombination region for holes and electrons can be confined within the light-emitting layer owing to the hole-trapping property acquired by providing different HOMO levels in the light-emitting layer. Thus, a light-emitting element having higher efficiency than a conventional light-emitting element can be obtained. Further, as a light-emitting device including the above light-emitting element, a passive matrix light-emitting device, an active matrix light-emitting device, and the like can be manufactured. Each of the above light-emitting devices is included in the present invention.

Note that there is no particular limitation on the structure of a TFT in the case of manufacturing the active matrix light-emitting device. For example, a staggered TFT or an inverted staggered TFT can be used as appropriate. Further, a driver circuit formed over a TFT substrate may be formed using both an n-type TFT and a p-type TFT or either an n-type TFT or a p-type TFT. Furthermore, there is also no particular limitation on the crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

Embodiment 2

In this embodiment, novel pyrene-based compounds which are embodiments of the present invention and can be used in the light-emitting element described in Embodiment 1 will be described.

One embodiment of the present invention is a pyrene-based compound having a structure represented by the following general formula (G1).

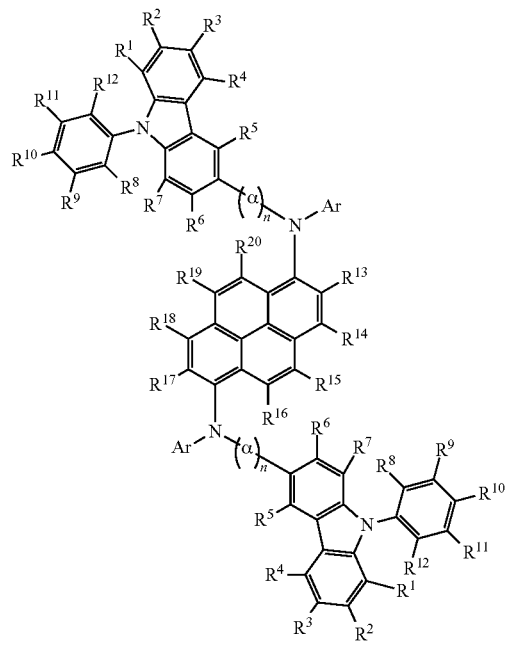

(G1)

In the general formula (G1), Ar represents a substituted or unsubstituted aryl group having 6 to 10 carbon atoms, α represents a substituted or unsubstituted phenylene group, and $R^1$ to $R^{12}$ separately represent a hydrogen atom or an alkyl group having 1 to 4 carbon atoms. Further, $R^{13}$ to $R^{20}$ separately represent a hydrogen atom or an alkyl group having 1 to 6 carbon atoms. Further, n is 0 or 1.

Here, specific examples of ac include a phenylene group and a phenylene group substituted by one or more alkyl groups each having 1 to 4 carbon atoms.

Note that n is preferably equal to 0 in the above general formula (G1) for easier synthesis. Thus, another embodiment of the present invention is a pyrene-based compound including a structure represented by the following general formula (G2).

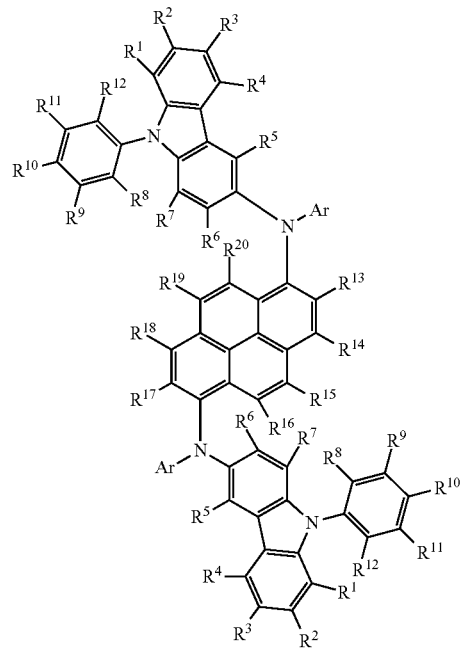

(G2)

In the general formula (G2), Ar represents a substituted or unsubstituted aryl group having 6 to 10 carbon atoms, and $R^1$ to $R^{12}$ separately represent a hydrogen atom or an alkyl group having 1 to 4 carbon atoms. Further, $R^{13}$ to $R^{20}$ separately represent a hydrogen atom or an alkyl group having 1 to 6 carbon atoms.

Among pyrene-based compounds including the structure represented by the general formula (G2), a pyrene-based compound represented by the following general formula (G3) is preferable.

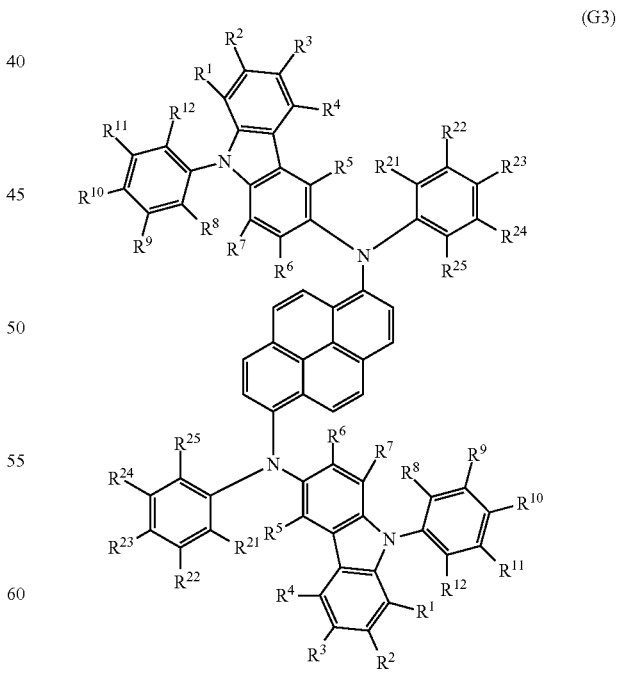

(G3)

In the general formula (G3), $R^1$ to $R^{12}$ and $R^{21}$ to $R^{25}$ separately represent a hydrogen atom or an alkyl group having 1 to 4 carbon atoms.

In the general formulae (G1) to (G3), specific examples of the alkyl group having 1 to 4 carbon atoms for any of R to $R^{12}$ include a methyl group, an ethyl group, a propyl group, an isopropyl group, a butyl group, a sec-butyl group, an isobutyl group, a tert-butyl group, and the like. Specific examples of the alkyl group having 1 to 6 carbon atoms for any of $R^{13}$ to $R^{20}$ include a methyl group, an ethyl group, a propyl group, an isopropyl group, a butyl group, a sec-butyl group, an isobutyl group, a tert-butyl group, a pentyl group, an isopentyl group, a hexyl group, a cyclohexyl group, and the like.

Next, specific structural formulae of the pyrene-based compounds which are embodiments of the present invention are shown (the following structural formulae (100) to (114)). Note that the present invention is not limited thereto.

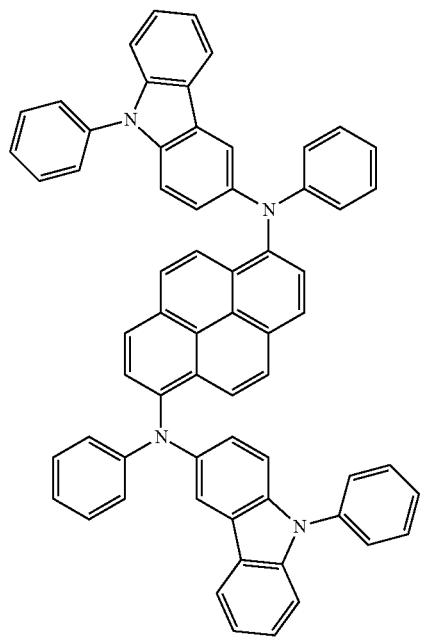

(100)

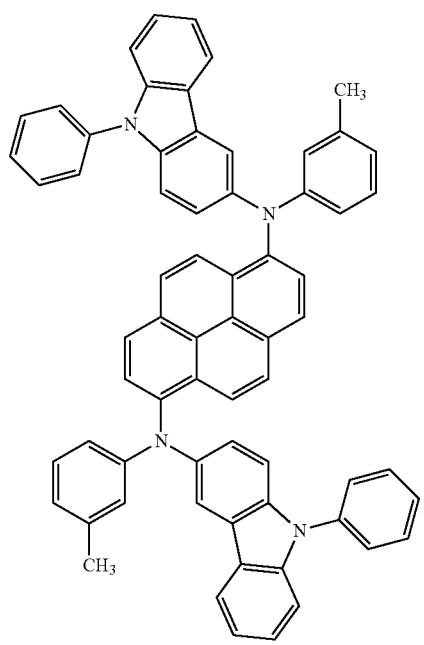

(101)

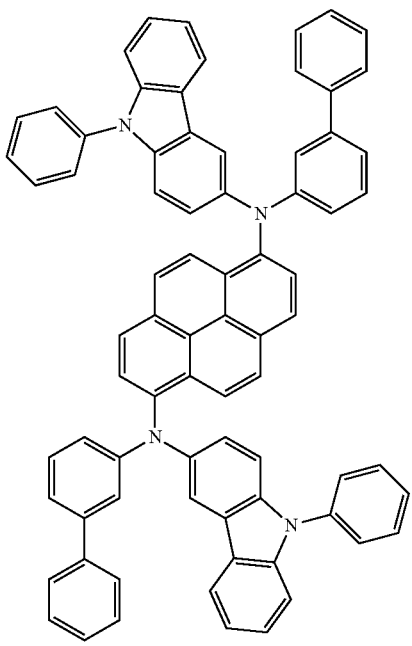

(102)

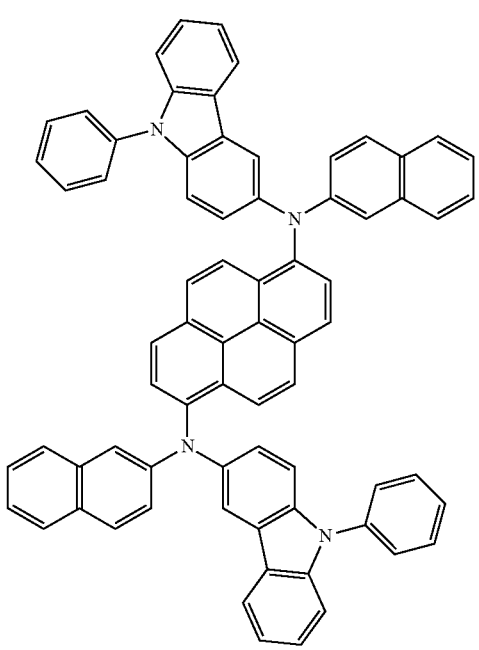

(103)

(104)
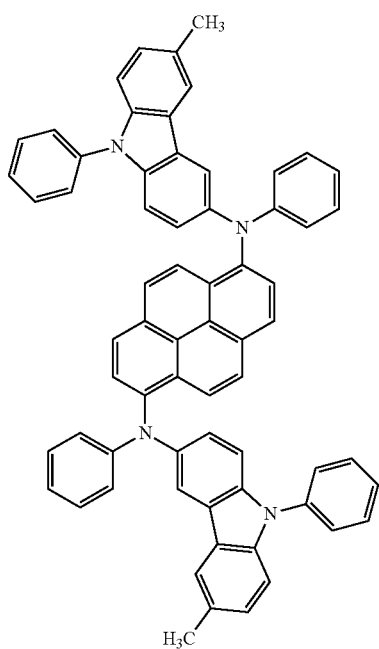
(105)
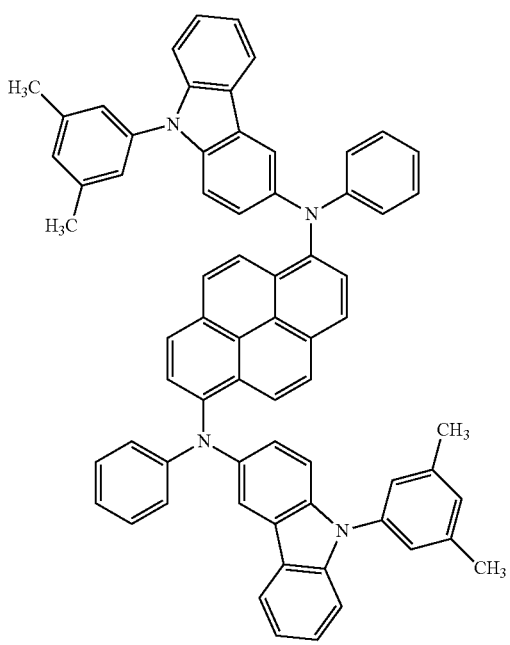
(106)
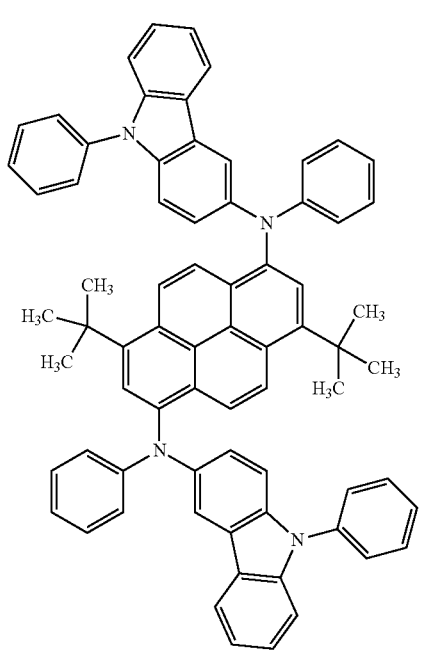
(107)
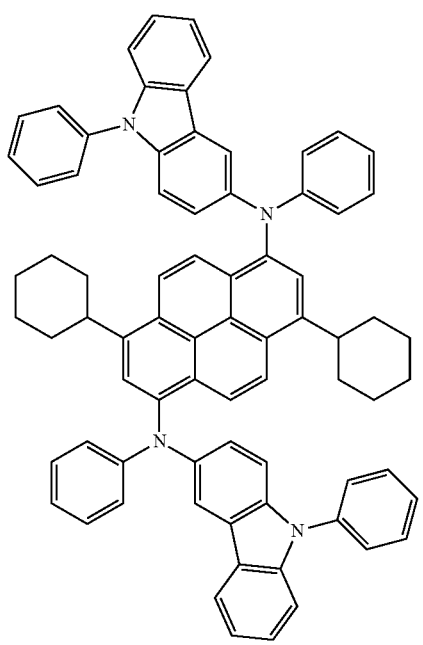

(108)
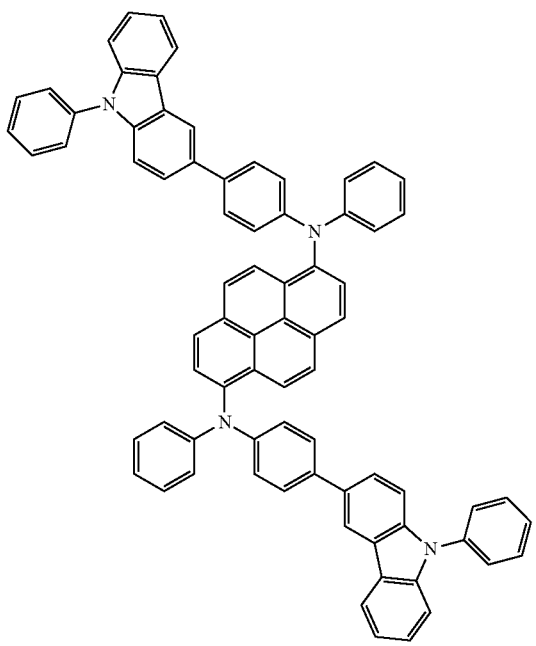
(109)
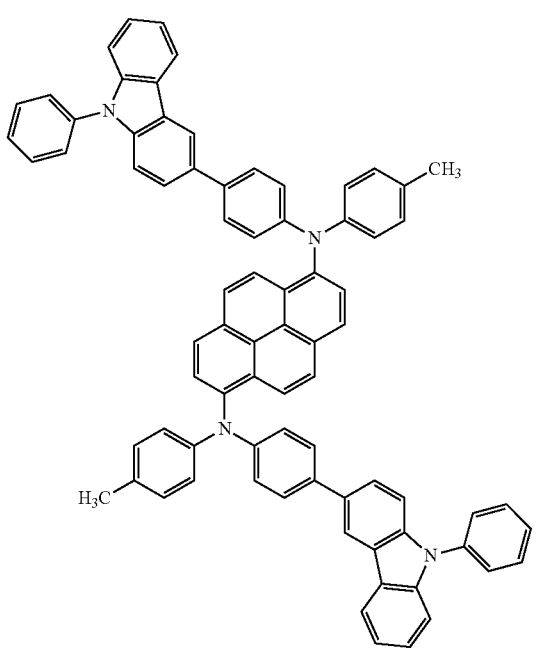
(110)
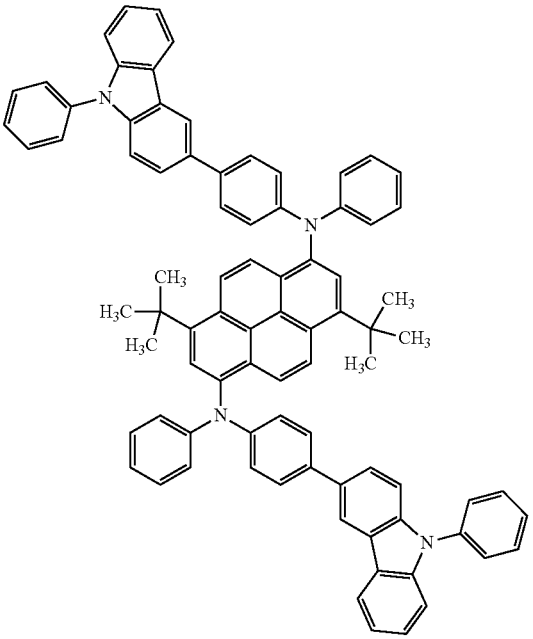
(111)
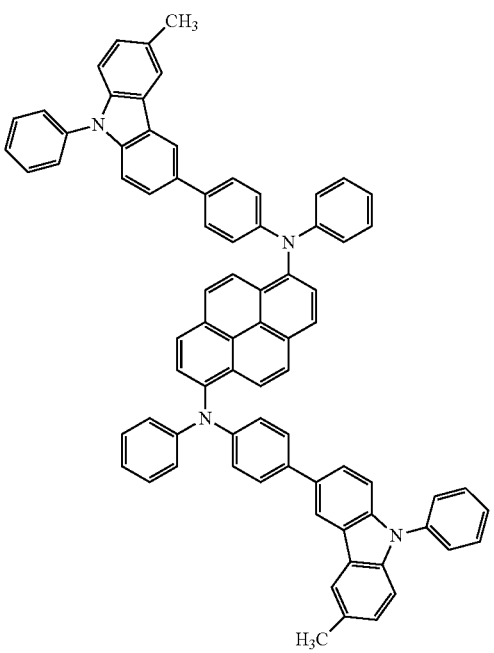

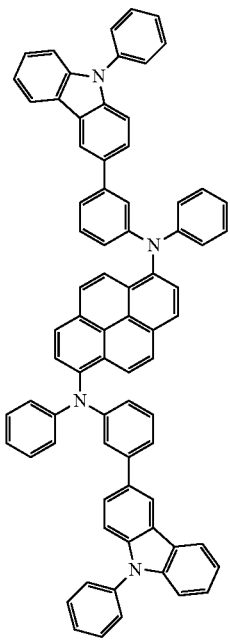

(112)

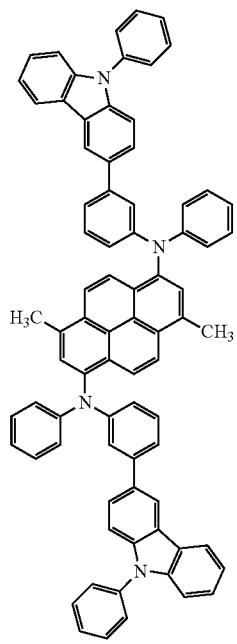

(114)

A variety of reactions can be applied to methods of synthesizing the above-described novel pyrene-based compounds which are embodiments of the present invention. For example, the pyrene-based compound which is one embodiment of the present invention and represented by the general formula (G1) can be synthesized by synthesis reactions described below. Note that methods of synthesizing the novel pyrene-based compounds which are embodiments of the present invention are not limited to the synthesis methods described below.

((Method of Synthesizing Pyrene-based Compound Represented by General Formula (G1)))

An example of a method of synthesizing the pyrene-based compound represented by the following general formula (G1) will be described.

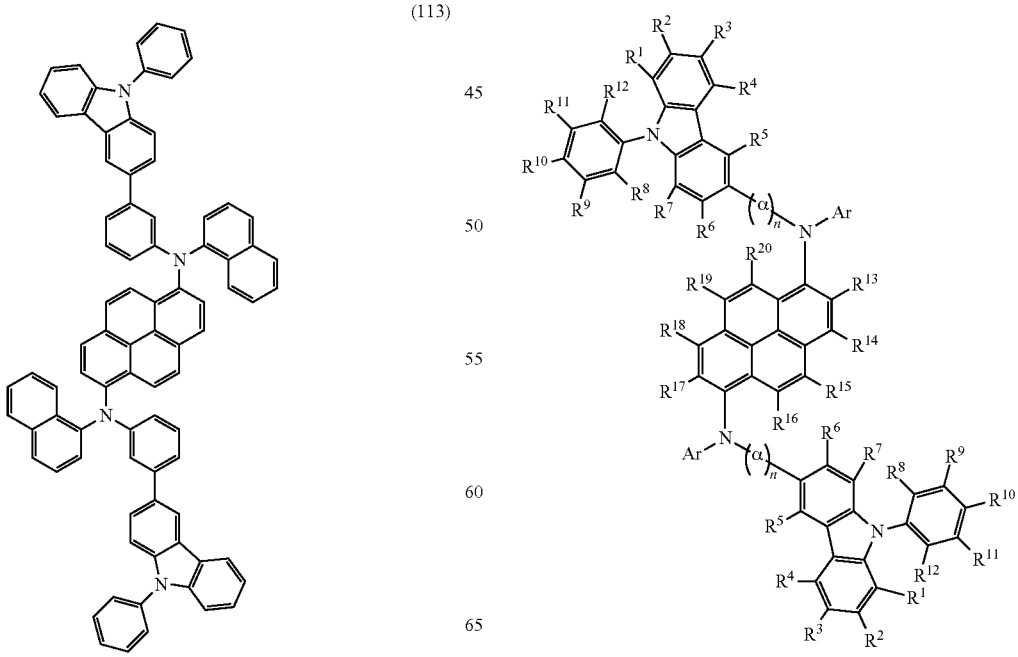

(113)

(G1)

As illustrated in the following synthesis scheme (A-1), a halide of a carbazole derivative (a1) and an aryl compound having an amine (a2) are coupled, whereby an amine derivative (a3) can be obtained.

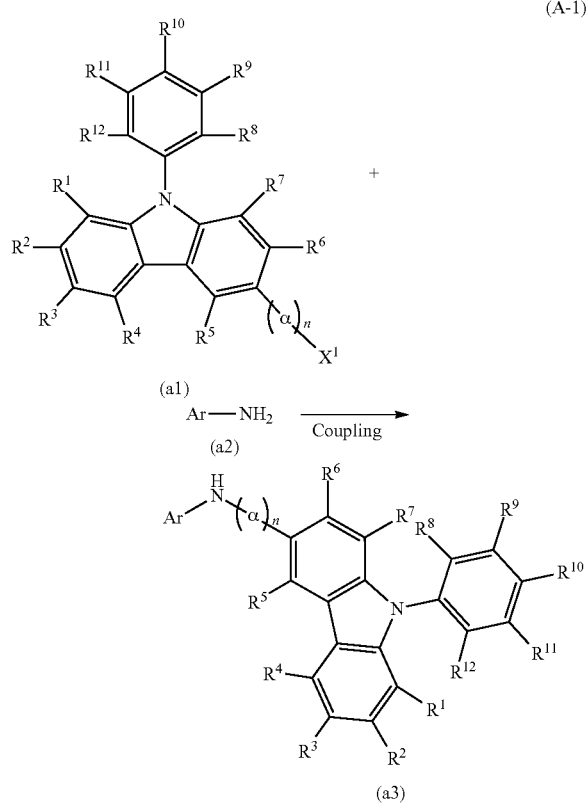

(A-1)

Note that in the synthesis scheme (A-1), Ar represents a substituted or unsubstituted aryl group having 6 to 10 carbon atoms. Further, $R^1$ to $R^{12}$ separately represent a hydrogen atom or an alkyl group having 1 to 4 carbon atoms. Further, α represents a substituted or unsubstituted phenylene group. Further, n is 0 or 1. Further, $X^1$ represents a halogen, preferably bromine or iodine, more preferably iodine, which has high reactivity.

In the synthesis scheme (A-1), the aryl compound having an amine (a primary arylamine compound or a secondary arylamine compound) and the halide of a carbazole derivative may be coupled by a variety of synthesis methods under a variety of reaction conditions. As an example thereof, a synthesis method using a metal catalyst in the presence of a base (e.g., the Hartwig-Buchwald reaction or the Ullmann reaction) can be employed.

Then, the case where the Hartwig-Buchwald reaction is performed in the synthesis scheme (A-1) is described. As the metal catalyst, a palladium catalyst can be used, and as the palladium catalyst, a mixture of a palladium complex and a ligand thereof can be used. Specific examples of the palladium complex include bis(dibenzylideneacetone)palladium (0), palladium(II) acetate, and the like. Examples of the ligand include tri(tert-butyl)phosphine, tri(n-hexyl)phosphine, tricyclohexylphosphine, 1,1-bis(diphenylphosphino)ferrocene (abbreviation: DPPF), and the like. Examples of a substance which can be used as the base include organic bases such as sodium tert-butoxide, inorganic bases such as potassium carbonate, and the like.

Note that the reaction is preferably performed in a solution. Examples of a solvent which can be used include toluene, xylene, benzene, and the like. However, the catalyst, ligand, base, and solvent which can be used are not limited thereto. In addition, the reaction is preferably performed under an inert atmosphere of nitrogen, argon, or the like.

Next, the case where the Ullmann reaction is performed in the synthesis scheme (A-1) is described. As the metal catalyst, a copper catalyst can be used, and specifically, copper(I) iodide or copper(II) acetate can be used. Examples of a substance which can be used as the base include inorganic bases such as potassium carbonate.

This reaction is also preferably performed in a solution. Examples of a solvent which can be used include 1,3-dimethyl-3,4,5,6-tetrahydro-2(1H)-pyrimidinone (DMPU), toluene, xylene, benzene, and the like. However, the catalyst, base, and solvent which can be used are not limited thereto. In addition, the reaction is preferably performed under an inert atmosphere of nitrogen, argon, or the like.

Note that a solvent having a high boiling point such as DMPU or xylene is preferably used because, in the Ullmann reaction, an object can be obtained in a shorter time and in a higher yield when the reaction temperature is 100° C. or higher. In particular, DMPU is more preferable because the reaction temperature is more preferably 150° C. or higher.

Next, a synthesis scheme (A-2) is shown. As illustrated in the following synthesis scheme (A-2), the amine derivative (a3) and a halogenated pyrene derivative (a4) are coupled, whereby the amine derivative represented by the general formula (G1) can be obtained.

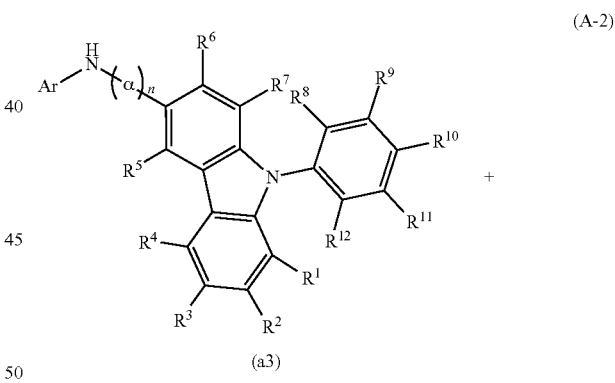

(A-2)

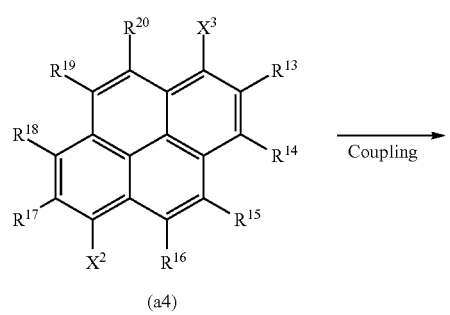

-continued

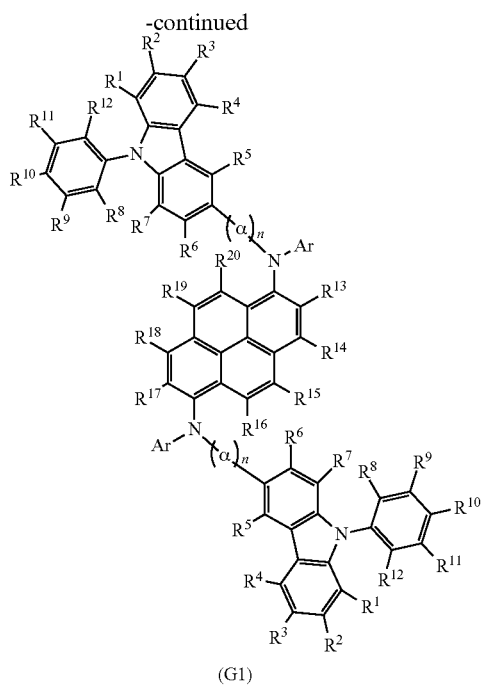

(G1)

Note that in the synthesis scheme (A-2), Ar represents a substituted or unsubstituted aryl group having 6 to 10 carbon atoms. Further, $R^1$ to $R^{12}$ separately represent a hydrogen atom or an alkyl group having 1 to 4 carbon atoms. Further, $R^{13}$ to $R^{20}$ separately represent a hydrogen atom or an alkyl group having 1 to 6 carbon atoms. Further, α represents a substituted or unsubstituted phenylene group. Further, n is 0 or 1. Further, $X^2$ and $X^3$ each represent a halogen. Note that the halogen is preferably bromine or iodine, more preferably iodine, which has high reactivity.

In the synthesis scheme (A-2), two equivalents of the amine derivative (a3) are reacted with the halogenated pyrene derivative (a4).

Also in the synthesis scheme (A-2), the aryl compound having an amine (a primary arylamine compound or a secondary arylamine compound) and the aryl compound having a halogen group may be coupled by a variety of synthesis methods under a variety of reaction conditions, as in the synthesis scheme (A-1). As an example thereof, a synthesis method using a metal catalyst in the presence of a base (e.g., the Hartwig-Buchwald reaction or the Ullmann reaction) can be employed.

One example of the method of synthesizing the pyrene-based compound (G1) which is one embodiment of the present invention is described above; however, the present invention is not limited thereto and any other synthesis method may be employed.

With the use of the pyrene-based compound that is one embodiment of the present invention, a light-emitting element, a light-emitting device, an electronic device, or a lighting device having high emission efficiency can be obtained. Furthermore, a light-emitting element, a light-emitting device, an electronic device, or a lighting device having low power consumption can be obtained.

The structure described in this embodiment can be combined as appropriate with any of the structures described in the other embodiments.

Embodiment 3

In this embodiment, as one embodiment of the present invention, a light-emitting element (hereinafter referred to as tandem light-emitting element) in which a charge generation layer is provided between a plurality of EL layers will be described.

Figure 2A:
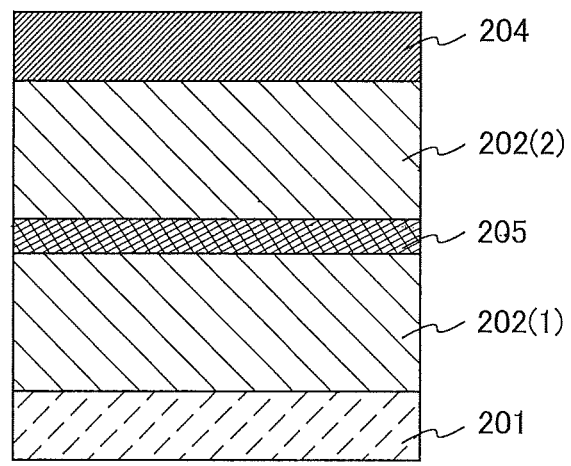
FIGS. 2A and 2B each illustrate a structure of a light-emitting element.

The light-emitting element described in this embodiment is a tandem light-emitting element including a plurality of EL layers (a first EL layer 202(1) and a second EL layer 202(2)) between a pair of electrodes (a first electrode 201 and a second electrode 204) as illustrated in FIG. 2A.

In this embodiment, the first electrode 201 functions as an anode, and the second electrode 204 functions as a cathode. Note that the first electrode 201 and the second electrode 204 can have structures similar to those described in Embodiment 1. In addition, all or any of the plurality of EL layers (the first EL layer 202(1) and the second EL layer 202(2)) may have structures similar to those described in Embodiment 1. In other words, the structures of the first EL layer 202(1) and the second EL layer 202(2) may be the same or different from each other and can be similar to those of the EL layers described in Embodiment 1. Note that the pyrene-based compound which is one embodiment of the present invention and described in Embodiment 2 can be used for any or all of the plurality of EL layers (the first EL layer 202(1) and the second EL layer 202(2)) described in this embodiment.

Further, a charge generation layer (I) 205 is provided between the plurality of EL layers (the first EL layer 202(1) and the second EL layer 202(2)). The charge generation layer (I) 205 has a function of injecting electrons into one of the EL layers and injecting holes into the other of the EL layers when a voltage is applied between the first electrode 201 and the second electrode 204. In this embodiment, when a voltage is applied such that the potential of the first electrode 201 is higher than that of the second electrode 204, the charge generation layer (I) 205 injects electrons into the first EL layer 202(1) and injects holes into the second EL layer 202(2).

Note that in terms of light extraction efficiency, the charge generation layer (I) 205 preferably has a light-transmitting property with respect to visible light (specifically, the charge generation layer (I) 205 preferably has a visible light transmittance of 40% or more). Further, the charge generation layer (I) 205 functions even if it has lower conductivity than the first electrode 201 or the second electrode 204.

The charge generation layer (I) 205 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case where the electron acceptor is added to the organic compound having a high hole-transport property, examples of the organic compound having a high hole-transport property include aromatic amine compounds such as NPB, TPD, TDATA, MTDATA, and 4,4'-bis[N-(spiro-9,9'-bifluoren-2-yl)-N-phenylamino]biphenyl (abbreviation: BSPB), and the like. The substances mentioned here are mainly substances that have a hole mobility of $10^{-6}$ cm$^2$/Vs or more. Note that other than these substances, any organic compound that has a property of transporting more holes than electrons may be used.

Examples of the electron acceptor are 7,7,8,8-tetracyano-2,3,5,6-tetrafluoroquinodimethane (abbreviation: F$_4$-TCNQ), chloranil, oxides of transition metals, and oxides of metals that belong to Groups 4 to 8 of the periodic table. Specifically, vanadium oxide, niobium oxide, tantalum oxide, chromium oxide, molybdenum oxide, tungsten oxide, manganese oxide, and rhenium oxide are preferable because of their high electron-accepting property. Among these, molybdenum oxide is especially preferable since it is stable in the air, has a low hygroscopic property, and is easy to handle.

On the other hand, in the case where the electron donor is added to the organic compound having a high electron-transport property, examples of the organic compound having a high electron-transport property which can be used are metal complexes having a quinoline skeleton or a benzoquinoline skeleton, such as Alq, Almq$_3$, BeBq$_2$, and BAlq, and the like. Other examples are metal complexes having an oxazole-based or thiazole-based ligand, such as Zn(BOX)$_2$ and Zn(BTZ)$_2$. Other than metal complexes, PBD, OXD-7, TAZ, BPhen, BCP, or the like can be used. The substances mentioned here are mainly substances that have an electron mobility of $10^{-6}$ cm$^2$/Vs or more. Note that other than these substances, any organic compound that has a property of transporting more electrons than holes may be used.

Examples of the electron donor which can be used are alkali metals, alkaline earth metals, rare earth metals, metals that belong to Groups 2 and 13 of the periodic table, and oxides or carbonates thereof. Specifically, lithium (Li), cesium (Cs), magnesium (Mg), calcium (Ca), ytterbium (Yb), indium (In), lithium oxide, cesium carbonate, and the like are preferable. An organic compound, such as tetrathianaphthacene, may be used as the electron donor.

Note that forming the charge generation layer (I) 205 by using any of the above materials can suppress a drive voltage increase caused by the stack of the EL layers.

Figure 2B:
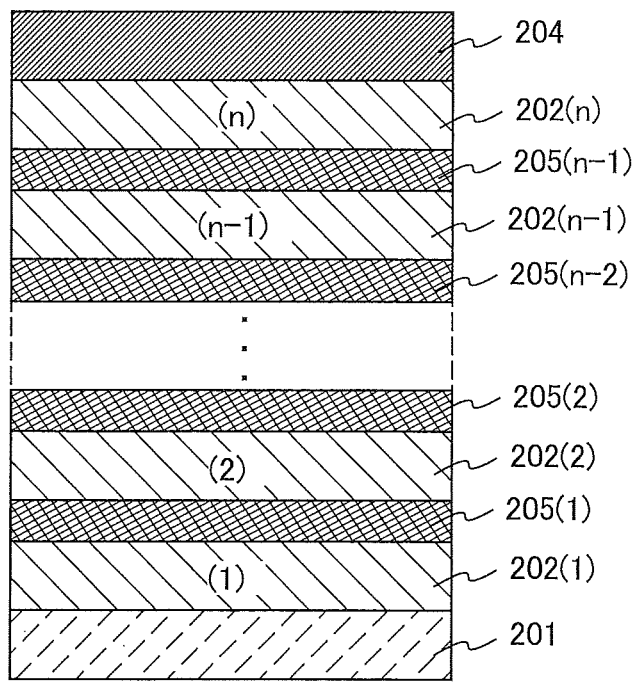

Although this embodiment shows the light-emitting element having two EL layers, the present invention can be similarly applied to a light-emitting element in which n EL layers (n is three or more) are stacked as illustrated in FIG. 2B. In the case where a plurality of EL layers is included between a pair of electrodes as in the light-emitting element according to this embodiment, by provision of the charge generation layer (I) between the EL layers, light emission in a high luminance region can be obtained with current density kept low. Since the current density can be kept low, the element can have a long lifetime. When the light-emitting element is applied to lighting, voltage drop due to resistance of an electrode material can be reduced, thereby achieving homogeneous light emission in a large area. Moreover, it is possible to achieve a light-emitting device which can be driven at a low voltage and has low power consumption.

Note that the structure described in this embodiment can be combined as appropriate with any of the structures described in the other embodiments.

Embodiment 4

In this embodiment, a light-emitting device including a light-emitting element which is one embodiment of the present invention will be described.

The light-emitting device can be either a passive matrix light-emitting device or an active matrix light-emitting device. Note that any of the light-emitting elements described in the other embodiments can be applied to the light-emitting device described in this embodiment.

In this embodiment, an active matrix light-emitting device is described with reference to FIGS. 3A and 3B.

Figure 3A:
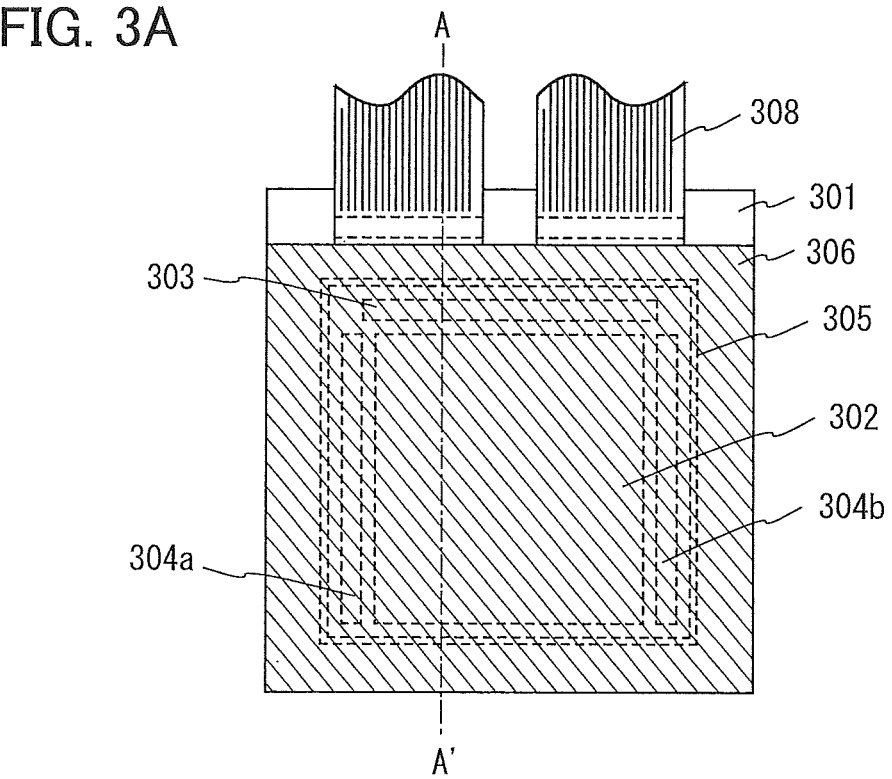
FIGS. 3A and 3B illustrate a light-emitting device.
Figure 3B:
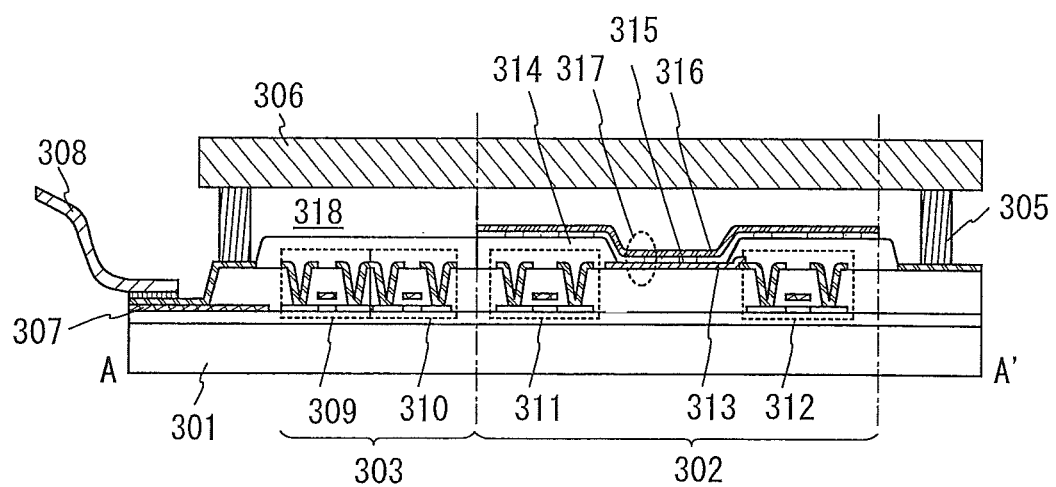

Note that FIG. 3A is a top view illustrating a light-emitting device and FIG. 3B is a cross-sectional view taken along the chain line A-A' in FIG. 3A. The active matrix light-emitting device according to this embodiment includes a pixel portion 302 provided over an element substrate 301, a driver circuit portion (a source line driver circuit) 303, and driver circuit portions (gate line driver circuits) 304a and 304b. The pixel portion 302, the driver circuit portion 303, and the driver circuit portions 304a and 304b are sealed between the element substrate 301 and a sealing substrate 306 with a sealant 305.

In addition, there is provided a lead wiring 307 over the element substrate 301. The lead wiring 307 is provided for connecting an external input terminal through which a signal (e.g., a video signal, a clock signal, a start signal, and a reset signal) or a potential from the outside is transmitted to the driver circuit portion 303 and the driver circuit portions 304a and 304b. Here is shown an example in which a flexible printed circuit (FPC) 308 is provided as the external input terminal. Although only the FPC 308 is illustrated, this FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 3B. The driver circuit portions and the pixel portion are formed over the element substrate 301; here are illustrated the driver circuit portion 303 which is the source line driver circuit and the pixel portion 302.

The driver circuit portion 303 is an example where a CMOS circuit is formed, which is a combination of an n-channel TFT 309 and a p-channel TFT 310. Note that a circuit included in the driver circuit portion may be formed using any of various circuits, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 302 includes a plurality of pixels each of which includes a switching TFT 311, a current control TFT 312, and a first electrode (anode) 313 which is electrically connected to a wiring (a source electrode or a drain electrode) of the current control TFT 312. Note that an insulator 314 is formed to cover end portions of the first electrode (anode) 313. In this embodiment, the insulator 314 is formed using a positive photosensitive acrylic resin.

The insulator 314 preferably has a curved surface with curvature at an upper end portion or a lower end portion thereof in order to obtain favorable coverage by a film which is to be stacked over the insulator 314. For example, in the case of using a positive photosensitive acrylic resin as a material for the insulator 314, the insulator 314 preferably has a curved surface with a curvature radius (0.2 μm to 3 μm) at the upper end portion. The insulator 314 can be formed using either a negative photosensitive resin or a positive photosensitive resin. It is possible to use, without limitation to an organic compound, either an organic compound or an inorganic compound such as silicon oxide or silicon oxynitride.

An EL layer 315 and a second electrode (cathode) 316 are stacked over the first electrode (anode) 313. In the EL layer 315, at least a light-emitting layer is provided. The light-emitting layer has the stacked structure described in Embodiment 1. The pyrene-based compound described in Embodiment 2 can be used. Further, in the EL layer 315, a hole-injection layer, a hole-transport layer, an electron-transport layer, an electron-injection layer, a charge generation layer, and the like can be provided as appropriate in addition to the light-emitting layer.

The stacked structure of the first electrode (anode) 313, the EL layer 315, and the second electrode (cathode) 316 forms a light-emitting element 317. For the first electrode (anode) 313, the EL layer 315, and the second electrode (cathode) 316, the materials described in Embodiment 1 can be used. Although not illustrated, the second electrode (cathode) 316 is electrically connected to the FPC 308 which is an external input terminal.

Although the cross-sectional view of FIG. 3B illustrates only one light-emitting element 317, a plurality of light-emitting elements is arranged in matrix in the pixel portion 302. Light-emitting elements which provide three kinds of light emission (R, G, and B) are selectively formed in the pixel portion 302, whereby a light-emitting device capable of full color display can be fabricated. Alternatively, a light-emitting device capable of full color display may be fabricated by a combination with color filters.

Further, the sealing substrate 306 is attached to the element substrate 301 with the sealant 305, whereby the light-emitting element 317 is provided in a space 318 surrounded by the element substrate 301, the sealing substrate 306, and the sealant 305. The space 318 may be filled with an inert gas (such as nitrogen or argon) or the sealant 305.

An epoxy-based resin is preferably used for the sealant 305. It is preferable that such a material do not transmit moisture or oxygen as much as possible. As the sealing substrate 306, a glass substrate, a quartz substrate, or a plastic substrate formed of fiberglass reinforced plastic (FRP), polyvinyl fluoride (PVF), a polyester, an acrylic resin, or the like can be used.

As described above, an active matrix light-emitting device can be obtained.

Note that the structure described in this embodiment can be combined as appropriate with any of the structures described in the other embodiments.

Embodiment 5

In this embodiment, examples of a variety of electronic devices which are completed using a light-emitting device will be described with reference to FIGS. 4A to 4D and FIGS. 5A to 5C. The light-emitting device is fabricated using a light-emitting element which is one embodiment of the present invention.

Examples of electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices are illustrated in FIGS. 4A to 4D.

Figure 4A:
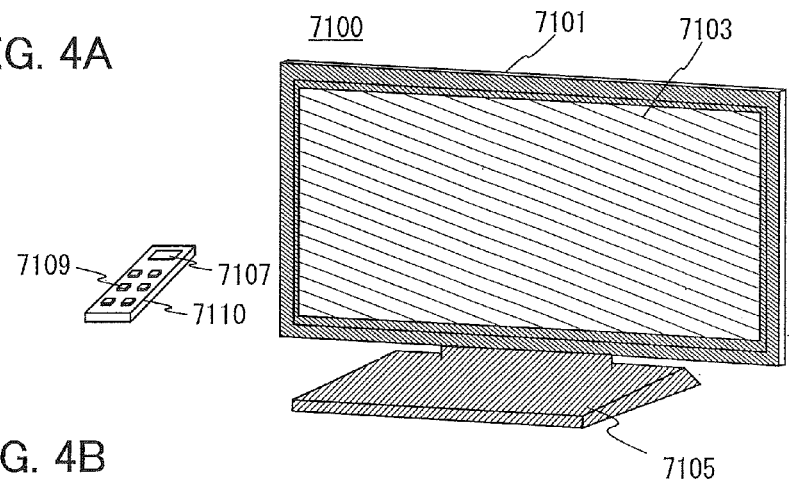
FIGS. 4A to 4D illustrate electronic devices.

FIG. 4A illustrates an example of a television device. In a television device 7100, a display portion 7103 is incorporated in a housing 7101. The display portion 7103 is capable of displaying images, and a light-emitting device can be used for the display portion 7103. In addition, here, the housing 7101 is supported by a stand 7105.

The television device 7100 can be operated with an operation switch provided in the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data to be output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 4B:
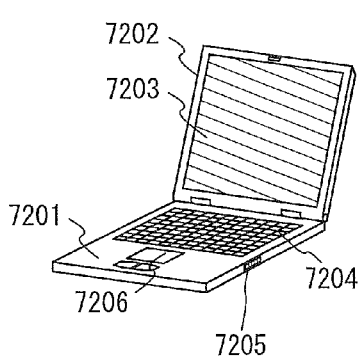

FIG. 4B illustrates a computer, which includes a main body 7201, a housing 7202, a display portion 7203, a keyboard 7204, an external connection port 7205, a pointing device 7206, and the like. Note that this computer is manufactured by using a light-emitting device for the display portion 7203.

Figure 4C:
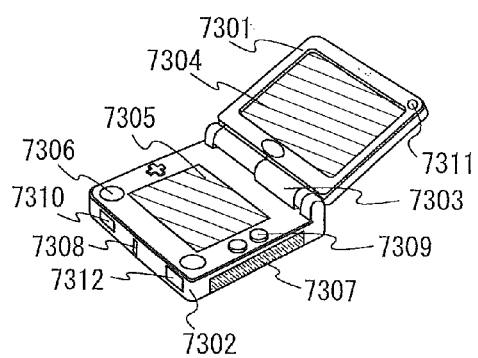

FIG. 4C illustrates a portable game machine, which includes two housings, i.e., a housing 7301 and a housing 7302, connected to each other via a joint portion 7303 so that the portable game machine can be opened or closed. A display portion 7304 is incorporated in the housing 7301 and a display portion 7305 is incorporated in the housing 7302. In addition, the portable game machine illustrated in FIG. 4C includes a speaker portion 7306, a recording medium insertion portion 7307, an LED lamp 7308, input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, electric current, voltage, electric power, radiation, flow rate, humidity, gradient, oscillation, odor, or infrared rays), and a microphone 7312), and the like. It is needless to say that the structure of the portable game machine is not limited to the above structure as long as a light-emitting device is used for at least either the display portion 7304 or the display portion 7305, or both, and may include other accessories as appropriate. The portable game machine illustrated in FIG. 4C has a function of reading out a program or data stored in a storage medium to display it on the display portion, and a function of sharing information with another portable game machine by wireless communication. Note that the portable game machine illustrated in FIG. 4C can have a variety of functions without limitation to those above.

Figure 4D:
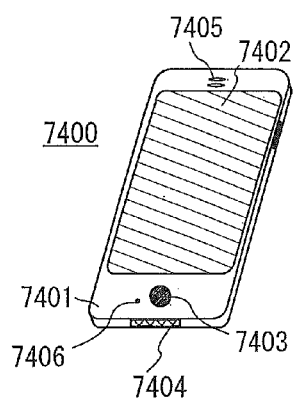

FIG. 4D illustrates an example of a cellular phone. A cellular phone 7400 is provided with a display portion 7402 incorporated in a housing 7401, operation buttons 7403, an external connection port 7404, a speaker 7405, a microphone 7406, and the like.

Note that the cellular phone 7400 is manufactured using a light-emitting device for the display portion 7402.

When the display portion 7402 of the cellular phone 7400 illustrated in FIG. 4D is touched with a finger or the like, data can be input to the cellular phone 7400. Further, operations such as making a call and creating e-mail can be performed by touch on the display portion 7402 with a finger or the like.

There are mainly three screen modes for the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are changed by touch on the display portion 7402 or operation with the operation buttons 7403 of the housing 7401. Alternatively, the screen modes can be changed depending on the kind of image displayed on the display portion 7402.

For example, when a signal for an image to be displayed on the display portion is data of moving images, the screen mode is changed to the display mode. When the signal is text data, the screen mode is changed to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal identification can be performed.

Furthermore, when a backlight or a sensing light source which emits near-infrared light is provided for the display portion, an image of a finger vein, a palm vein, or the like can also be taken.

Figure 5A:
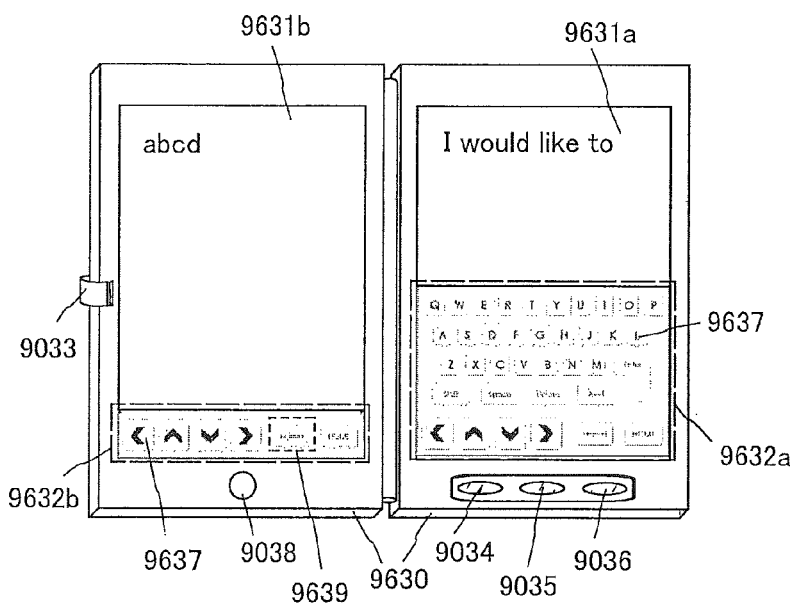
FIGS. 5A to 5C illustrate an electronic device.
Figure 5B:
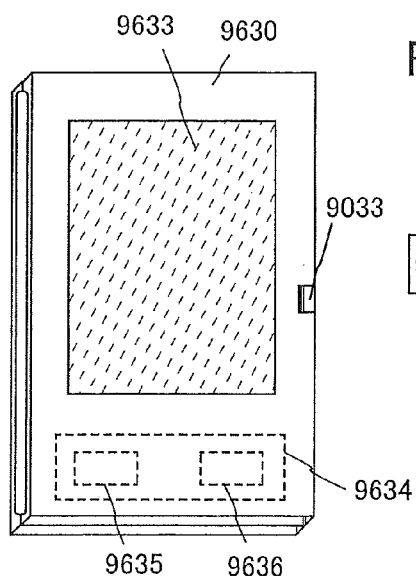

FIGS. 5A and 5B illustrate a foldable tablet terminal. The tablet terminal is opened in FIG. 5A. The tablet terminal includes a housing 9630, a display portion 9631*a*, a display portion 9631*b*, a display mode switch 9034, a power switch 9035, a power saver switch 9036, a clasp 9033, and an operation switch 9038. The tablet terminal is manufactured using the light-emitting device for either the display portion 9631*a* or the display portion 9361*b* or both.

Part of the display portion 9631*a* can be a touch panel region 9632*a* and data can be input when a displayed operation key 9637 is touched. Although a structure in which a half region in the display portion 9631*a* has only a display function and the other half region also has a touch panel function is shown as an example, the display portion 9631*a* is not limited to the structure. The whole region in the display portion 9631*a* may have a touch panel function. For example, the display portion 9631*a* can display keyboard buttons in the whole region to be a touch panel, and the display portion 9631*b* can be used as a display screen.

As in the display portion 9631*a*, part of the display portion 9631*b* can be a touch panel region 9632*b*. When a keyboard display switching button 9639 displayed on the touch panel is touched with a finger, a stylus, or the like, a keyboard can be displayed on the display portion 9361*b*.

Touch input can be performed in the touch panel region 9632*a* and the touch panel region 9632*b* at the same time.

The display mode switch 9034 can switch the display between portrait mode, landscape mode, and the like, and between monochrome display and color display, for example. The power saver switch 9036 can control display luminance in accordance with the amount of external light in use of the tablet terminal detected by an optical sensor incorporated in the tablet terminal. In addition to the optical sensor, another detection device including a sensor for detecting inclination, such as a gyroscope or an acceleration sensor, may be incorporated in the tablet terminal.

Note that FIG. 5A shows an example in which the display portion 9631*a* and the display portion 9361*b* have the same display area; however, without limitation thereon, one of the display portions may be different from the other display portion in size and display quality. For example, one display panel may be capable of higher-definition display than the other display panel.

The tablet terminal is closed in FIG. 5B. The tablet terminal includes the housing 9630, a solar cell 9633, a charge and discharge control circuit 9634, a battery 9635, and a DCDC converter 9636. In FIG. 5B, a structure including the battery 9635 and the DCDC converter 9636 is illustrated as an example of the charge and discharge control circuit 9634.

Since the tablet terminal is foldable, the housing 9630 can be closed when the tablet terminal is not used. As a result, the display portion 9631*a* and the display portion 9631*b* can be protected; thus, a tablet terminal which has excellent durability and excellent reliability in terms of long-term use can be provided.

In addition, the tablet terminal illustrated in FIGS. 5A and 5B can have a function of displaying a variety of kinds of data (e.g., a still image, a moving image, and a text image), a function of displaying a calendar, a date, the time, or the like on the display portion, a touch-input function of operating or editing the data displayed on the display portion by touch input, a function of controlling processing by a variety of kinds of software (programs), and the like.

The solar cell 9633 provided on a surface of the tablet terminal can supply power to the touch panel, the display portion, a video signal processing portion, or the like.

Note that a structure in which the solar cell 9633 is provided on one or both surfaces of the housing 9630 is preferable because the battery 9635 can be charged efficiently. The use of a lithium ion battery as the battery 9635 is advantageous in downsizing or the like.

The structure and the operation of the charge and discharge control circuit 9634 illustrated in FIG. 5B will be described with reference to a block diagram in FIG. 5C. The solar cell 9633, the battery 9635, the DCDC converter 9636, a converter 9638, switches SW1 to SW3, and the display portion 9631 are illustrated in FIG. 5C, and the battery 9635, the DCDC converter 9636, the converter 9638, and the switches SW1 to SW3 correspond to the charge and discharge control circuit 9634 illustrated in FIG. 5B.

First, an example of the operation in the case where power is generated by the solar cell 9633 using external light is described. The voltage of power generated by the solar battery is stepped up or down by the DCDC converter 9636 so that the power has a voltage for charging the battery 9635. Then, when the power from the solar cell 9633 is used for the operation of the display portion 9631, the switch SW1 is turned on and the voltage of the power is stepped up or down by the converter 9638 so as to be a voltage needed for the display portion 9631. In addition, when display on the display portion 9631 is not performed, the switch SW1 is turned off and the switch SW2 is turned on so that the battery 9635 may be charged.

Note that the solar cell 9633 is described as an example of a power generation means; however, without limitation thereon, the battery 9635 may be charged using another power generation means such as a piezoelectric element or a thermoelectric conversion element (Peltier element). For example, a non-contact electric power transmission module which transmits and receives power wirelessly (without contact) to charge the battery 9635, or a combination of the solar cell 9633 and another means for charge may be used.

Figure 5C:
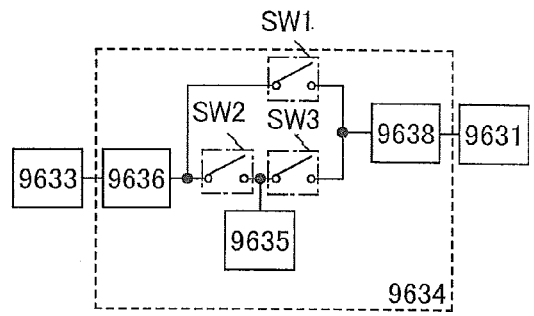

It is needless to say that an embodiment of the present invention is not limited to the electronic device illustrated in FIGS. 5A to 5C as long as the display portion described in the above embodiment is included.

As described above, the electronic devices can be obtained by the use of the light-emitting device which is one embodiment of the present invention. The light-emitting device has a remarkably wide application range, and can be applied to electronic devices in a variety of fields.

Note that the structure described in this embodiment can be combined as appropriate with any of the structures described in the other embodiments.

Embodiment 6

In this embodiment, examples of lighting devices will be described with reference to FIG. 6. A light-emitting device including a light-emitting element which is one embodiment of the present invention is applied to the lighting devices.

Figure 6:
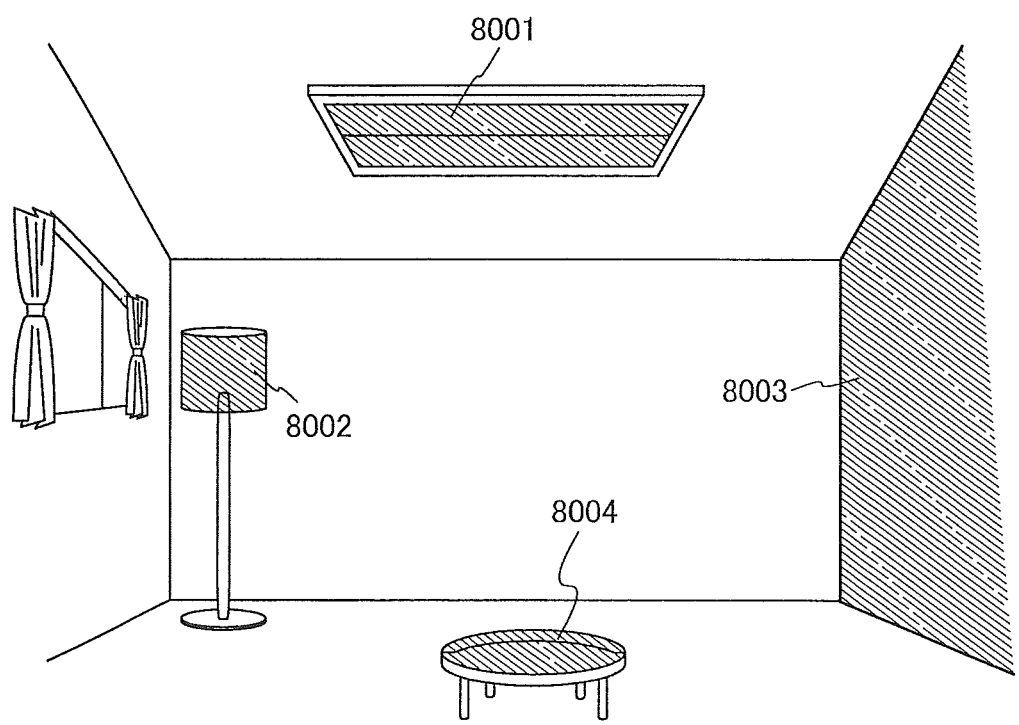
FIG. 6 illustrates lighting devices.

FIG. 6 illustrates an example in which a light-emitting device is used for an interior lighting device 8001. Since the light-emitting device can have a larger area, a lighting device having a large area can also be formed. In addition, a lighting device 8002 in which a light-emitting region has a curved surface can also be formed with the use of a housing with a curved surface. A light-emitting element included in the light-emitting device described in this embodiment is in the form of a thin film, which allows the housing to be designed more freely. Therefore, the lighting device can be elaborately designed in a variety of ways. Further, a wall of the room may be provided with a large-sized lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices to which the light-emitting device is applied can be obtained. Note that such lighting devices are also embodiments of the present invention.

The structure described in this embodiment can be combined as appropriate with any of the structures described in the other embodiments.

Example 1

Synthesis Example 1

In this example, a method of synthesizing N,N'-diphenyl-N,N'-(1,6-pyrenyl)-N,N'-bis(9-phenyl-9H-carbazol-3-yl)diamine (abbreviation: 1,6PCAPrn), the pyrene-based compound which is one embodiment of the present invention and represented by the structural formula (100) in Embodiment 2, will be described. Note that a structure of 1,6PCAPrn (abbreviation) is shown below.

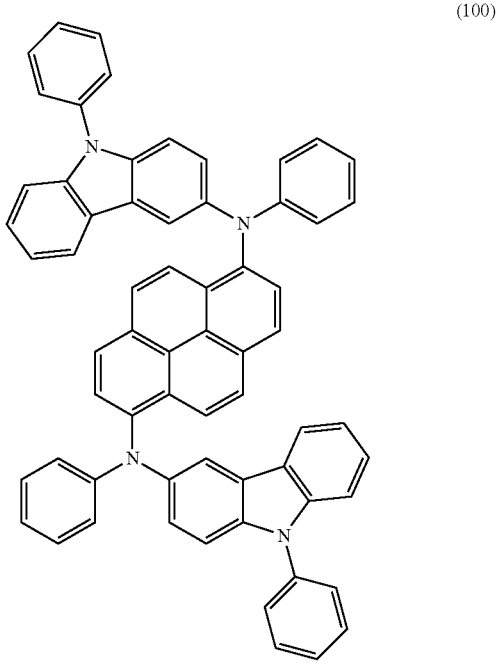 [SMILES: c1ccc(N(c2ccc3c(c2)c2ccccc2n3-c2ccccc2)c2ccc3ccc4c(N(c5ccccc5)c5ccc6c(c5)c5ccccc5n6-c5ccccc5)ccc5ccc2c3c54)cc1]

(100)

Synthesis of N,N'-Diphenyl-N,N'-(1,6-pyrenyl)-N,N'-bis(9-phenyl-9H-carbazol-3-yl)diamine (abbreviation: 1,6PCAPrn)

In a 100 mL three-neck flask were placed 0.80 g (2.2 mmol) of 1,6-dibromopyrene, 1.5 g (4.4 mmol) of N-phenyl-N-(9-phenyl-9H-carbazol-3-yl)amine, and 0.86 g (9.0 mmol) of sodium tert-butoxide. After the air in the flask was replaced with nitrogen, 25 mL of toluene and 2.2 mL of tri-tert-butylphosphine (a 10 wt % hexane solution) were added to the mixture.

While the pressure was reduced, this mixture was degassed by being stirred. After the degassing, 0.12 g (0.22 mmol) of bis(dibenzylideneacetone)palladium(0) was added to the mixture. This mixture was stirred at 110° C. for 7 hours under a nitrogen stream, so that a solid was precipitated. After the stirring, this mixture was subjected to suction filtration to give a solid.

The obtained solid was dissolved in about 500 mL of hot toluene, and this solution was subjected to suction filtration through Celite, alumina, and Florisil. The obtained filtrate was concentrated to give a solid. The obtained solid was recrystallized from chloroform/hexane to give 0.84 g of a target yellow powder solid in a yield of 43%.

In addition, by a train sublimation method, 0.84 g of the obtained yellow powder solid was purified. The sublimation purification was conducted under the conditions where the pressure was 3.5 Pa, the flow rate of an argon gas was 5.0 mL/min, and the heating temperature was 328° C. After the sublimation purification, 0.31 g of a yellow solid of 1,6PCAPrn was obtained in a collection rate of 37%.

The reaction scheme of the above synthesis method is illustrated in (a-1) below.

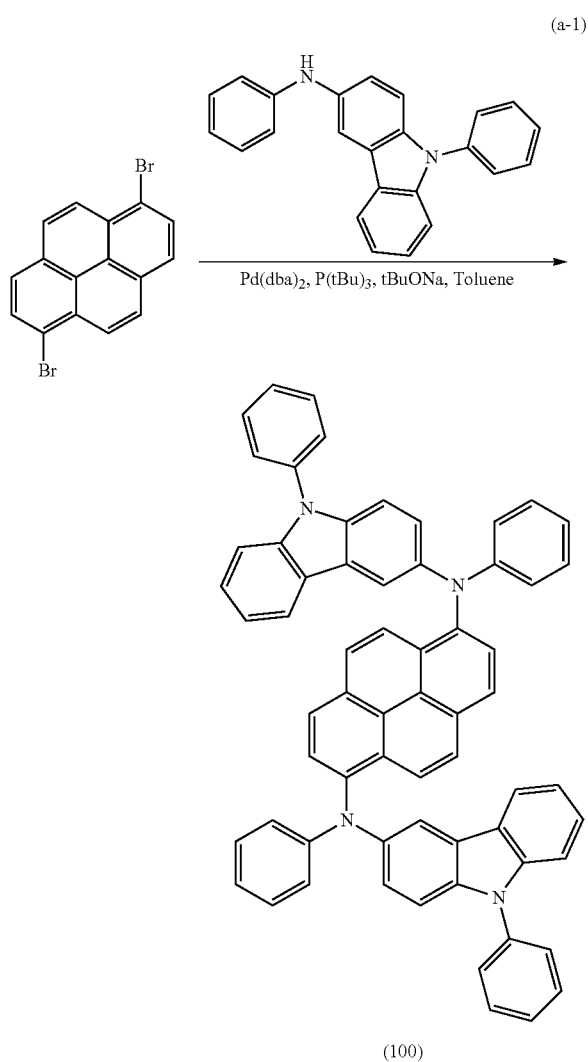

(100)

Figure 7A:
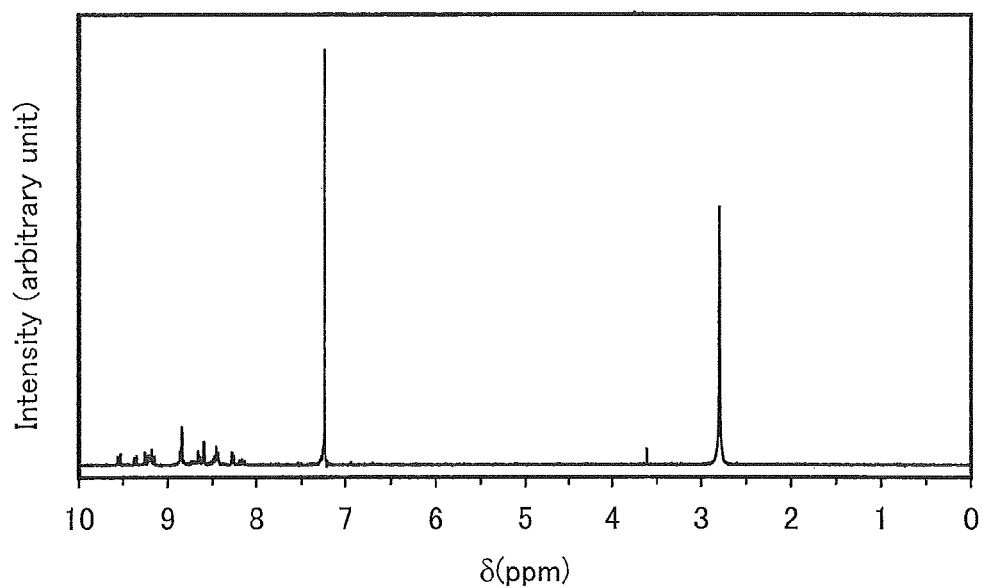
FIGS. 7A and 7B show $^1$H-NMR charts of a pyrene-based compound represented by a structural formula (100).
Figure 7B:
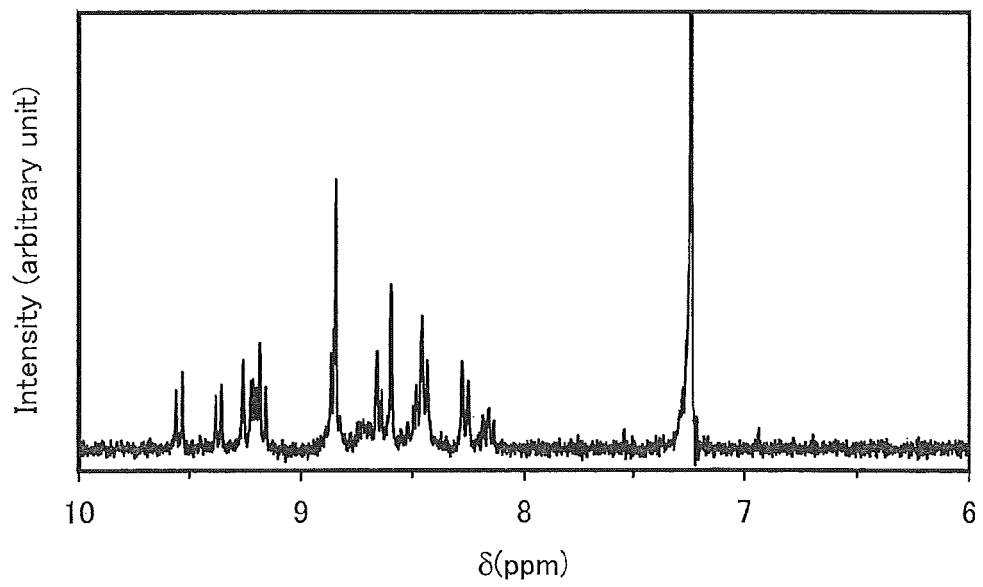

Results of nuclear magnetic resonance spectroscopy ($^1$H-NMR), by which the compound obtained by the above synthesis method was analyzed, are shown below. FIGS. 7A and 7B show the $^1$H-NMR charts. Note that FIG. 7B is an enlarged chart of FIG. 7A. The results reveal that N,N'-diphenyl-N,N'-(1,6-pyrenyl)-N,N'-bis(9-phenyl-9H-carbazol-3-yl)diamine (abbreviation: 1,6PCAPrn), the pyrene-based compound which is one embodiment of the present invention and represented by the above structural formula (100), was obtained.

$^1$H NMR (C$_2$H$_4$Cl$_4$, 300 MHz): δ=8.16 (t, J=7.2 Hz, 2H), 8.26 (d, J=8.4 Hz, 4H), 8.43-8.52 (m, 9H), 8.59-8.74 (m, 10H), 8.84-8.86 (m, 81H), 9.15-9.22 (m, 3H), 9.26 (s, 2H), 9.36 (d, J=8.1 Hz, 2H), 9.54 (d, J=8.7 Hz, 2H).

Next, 1,6PCAPrn (abbreviation) obtained in this example was analyzed by liquid chromatography mass spectrometry (LC/MS).

The analysis by LC/MS was carried out with Acquity UPLC (manufactured by Waters Corporation), and Xevo G2 Tof MS (manufactured by Waters Corporation).

In the MS analysis, ionization was carried out by an electrospray ionization (ESI) method. The capillary voltage and the sample cone voltage were set to 3.0 kV and 30 V, respectively. Detection was performed in a positive mode.

A component which underwent the ionization under the above conditions was collided with an argon gas in a collision cell to dissociate into a plurality of product ions. Energy (collision energy) for the collision with argon was 70 eV. The mass range for the measurement was m/z=100 to 1200.

Figure 21:
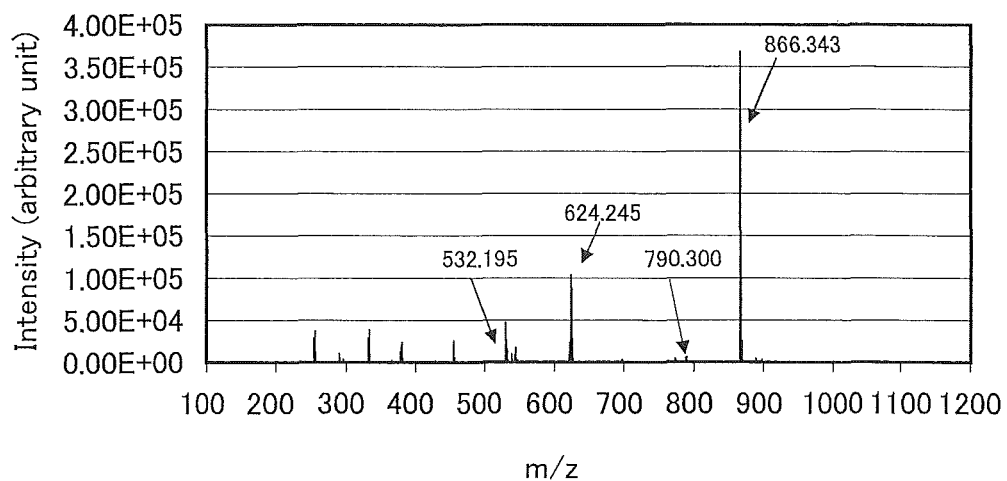
FIG. 21 shows results of LC-MS measurement of a heterocyclic compound represented by a structure formula (100).

FIG. 21 shows the measurement results. The results in FIG. 21 show that product ions of 1,6PCAPrn (abbreviation), the pyrene-based compound which is one embodiment of the present invention and represented by the structural formula (100), are detected mainly around m/z=790, m/z=624, and m/z=532.

The results in FIG. 21 are characteristically derived from 1,6PCAPrn (abbreviation) and thus can be regarded as important data in identification of 1,6PCAPrn (abbreviation) contained in a mixture.

Product ions around m/z=790 are presumed to be cations in the state where one phenyl group is dissociated from the compound of the structural formula (100). This is one of features of the pyrene-based compound which is one embodiment of the present invention. Product ions around m/z=624 are presumed to be cations in the state where one 9-phenyl-9H-carbazolyl group is dissociated from the compound of the structural formula (100), which indicates that the pyrene-based compound 1,6PCAPrn (abbreviation) which is one embodiment of the present invention includes a 9-phenyl-9H-carbazolyl group. Product ions around m/z=381 are presumed to be cations in the state where two phenyl groups are bound to pyrenediamine.

Next, ultraviolet-visible absorption spectra (hereinafter simply referred to as "absorption spectra") and emission spectra of 1,6PCAPrn (abbreviation) were measured. The absorption spectra were measured using an ultraviolet-visible light spectrophotometer (V550 type manufactured by JASCO Corporation). The emission spectra were measured using a fluorescence spectrophotometer (FS920 manufactured by Hamamatsu Photonics K.K.). The absorption spectra and the emission spectra of a toluene solution of 1,6PCAPrn (abbreviation) and a thin film of 1,6PCAPrn (abbreviation) were measured. Put in a quartz cell, the toluene solution was subjected to the measurement at room temperature. As for the thin film, the thin film which was deposited on a quartz substrate by evaporation was used. In order to obtain the absorption spectrum of the thin film, an absorption spectrum of quartz was subtracted from an absorption spectrum of the thin film and quartz.

Figure 8A:
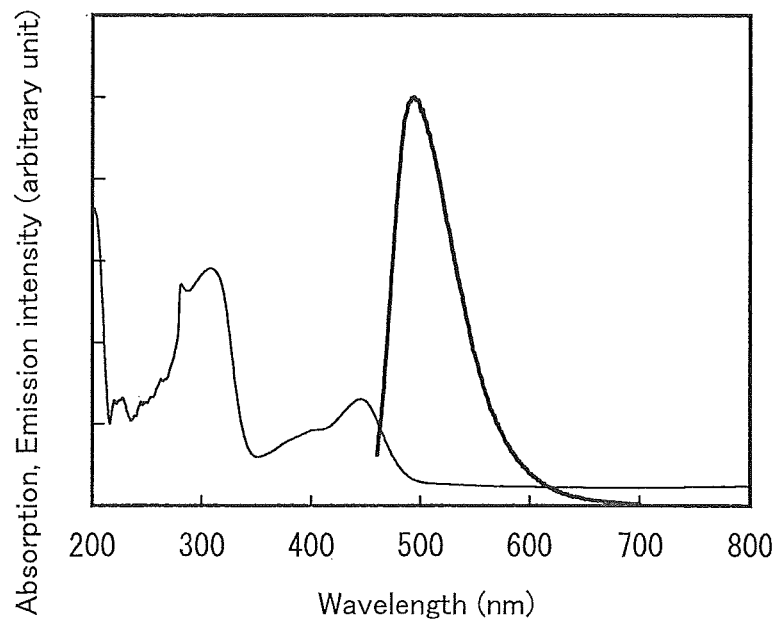
FIGS. 8A and 8B show ultraviolet-visible absorption spectra and emission spectra of the pyrene-based compound represented by the structural formula (100).
Figure 8B:
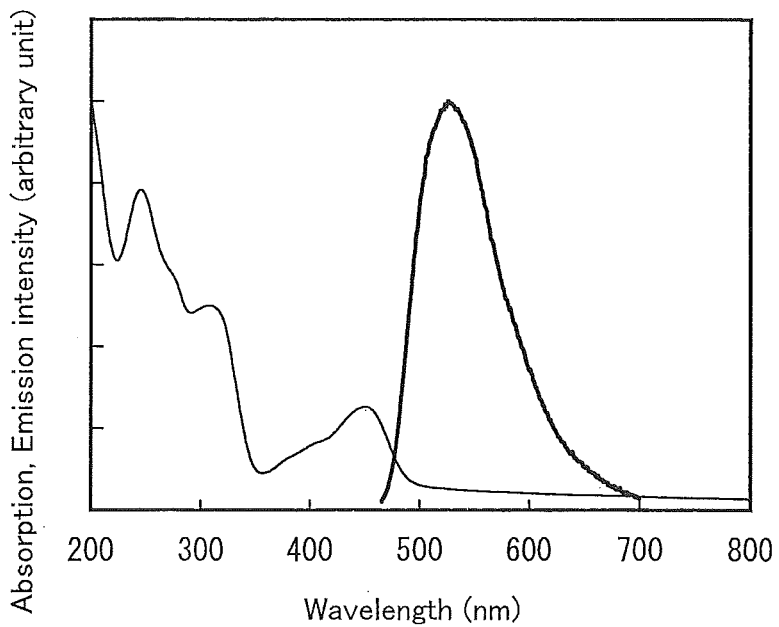

FIGS. 8A and 8B show measurement results of the absorption spectra and emission spectra. FIG. 8A shows the measurement results of the toluene solution of 1,6PCAPrn (abbreviation). FIG. 8B shows the measurement results of the thin film of 1,6PCAPrn (abbreviation). In each of FIGS. 8A and 8B, the horizontal axis represents wavelength (nm) and the vertical axis represents absorption intensity (arbitrary unit) or emission intensity (arbitrary unit). In each of FIGS. 8A and 8B, two solid lines are shown; a thin line represents the absorption spectrum, and a thick line represents the emission spectrum.

In the case of the toluene solution of 1,6PCAPrn (abbreviation), an absorption peak is observed at around 444 nm as shown in FIG. 8A. In the case of the thin film of 1,6PCAPrn (abbreviation), an absorption peak is observed at around 450 nm as shown in FIG. 8B.

Further, in the case of the toluene solution of 1,6PCAPrn (abbreviation), the maximum emission wavelength is 489 nm (excitation wavelength: 445 nm) as shown in FIG. 8A. In the case of the thin film of 1,6PCAPrn (abbreviation), the maximum emission wavelength is 526 nm (excitation wavelength: 450 nm) as shown in FIG. 8B.

As described above, 1,6PCAPm (abbreviation) was found to emit blue-green light with high color purity and accordingly can be used as a blue-green light-emitting material.

Further, the HOMO level and the LUMO level of 1,6PCAPrn (abbreviation) were obtained by cyclic voltammetry (CV) measurement. An electrochemical analyzer (ALS model 600A or 600C, manufactured by BAS Inc.) was used for the CV measurement.

Further, as for the solution used for the CV measurement, dehydrated dimethylformamide (DMF, manufactured by Sigma-Aldrich Inc., 99.8%, Catalog No. 22705-6) was used as a solvent, and tetra-n-butylammonium perchlorate (n-Bu$_4$NClO$_4$, manufactured by Tokyo Chemical Industry Co., Ltd., Catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 2 mmol/L.

A platinum electrode (PTE platinum electrode, manufactured by BAS Inc.) was used as a working electrode, a platinum electrode (Pt counter electrode for VC-3 (5 cm), manufactured by BAS Inc.) was used as an auxiliary electrode, and an Ag/Ag$^+$ electrode (RE-7 reference electrode for nonaqueous solvent, manufactured by BAS Inc.) was used as a reference electrode. The CV measurement was performed under the following conditions: room temperature (20° C. to 25° C.) and a scan rate of 0.1 V/sec. Note that the potential energy of the reference electrode with respect to the vacuum level was assumed to be −4.94 eV in this example.

On the assumption that the intermediate potential (the half-wave potential) between the oxidation peak potential $E_{pa}$ and the reduction peak potential $E_{pe}$ which are obtained in the CV measurement corresponds to the HOMO level, the HOMO level of 1,6PCAPrn (abbreviation) was calculated to be −5.32 eV, and the LUMO level of 1,6PCAPrn (abbreviation) was calculated to be −2.75 eV.

Note that 1,6PCAPrn (abbreviation) synthesized in this example and another pyrene-based compound having a different HOMO level but having substantially the same LUMO level are used to form a stack-type light-emitting layer. The stacked-type light-emitting layer has a hole-trapping property at the interface between the stacked light-emitting layers but is unlikely to block electron transfer.

Example 2

Synthesis Example 2

In this example, a method of synthesizing N,N'-diphenyl-N,N'-(1,6-pyrenyl)-N,N'-bis[4-(9-phenyl-9H-carbazol-3-yl)phenyl]diamine (abbreviation: 1,6PCBAPrn), the pyrene-based compound which is one embodiment of the present invention and represented by the structural formula (108) in Embodiment 2, will be described. Note that a structure of 1,6PCBAPrn (abbreviation) is shown below.

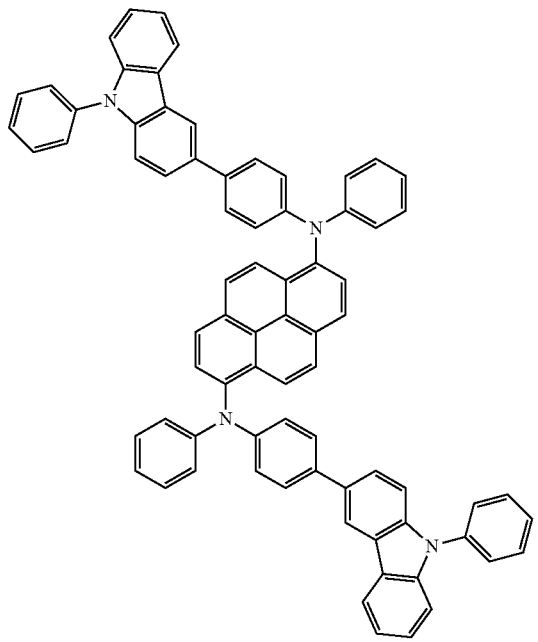

(108)

Synthesis of N,N'-Diphenyl-N,N'-(1,6-pyrenyl)-N,N'-bis[4-(9-phenyl-9H-carbazol-3-yl)phenyl]diamine (abbreviation: 1,6PCBAPrn)

In a 50 mL three-neck flask were placed 0.4 g (1.2 mmol) of 1,6-dibromopyrene, 1.5 g (3.5 mmol) of 4-(9-phenyl-9H-carbazol-3-yl)diphenylamine, and 0.5 g (5.3 mmol) of sodium tert-butoxide. The air in the flask was replaced with nitrogen.

Then, 17.7 mL of toluene and 0.2 mL of a 10% hexane solution of tri(tert-butyl)phosphine were added to this mixture. The temperature of this mixture was set to 80° C., 33.4 mg (0.05 mmol) of bis(dibenzylideneacetone)palladium(0) was added, and the mixture was stirred for 4.0 hours. Then, 22.4 mg (0.04 mmol) of bis(dibenzylideneacetone)palladium(0) was added, and the mixture was stirred for 0.5 hours. After the stirring, the mixture was subjected to suction filtration through Florisil, Celite, and alumina to give a filtrate.

The filtrate was concentrated to give a solid, which was then purified by silica gel column chromatography (the developing solvent has a 3:2 ratio of hexane to toluene). The obtained fractions were concentrated to give a target yellow solid. The obtained solid was recrystallized from chloroform/hexane to give 1.1 g of a yellow solid in a yield of 90%.

By a train sublimation method, 0.8 g of the obtained yellow solid was purified. The sublimation purification was conducted under the conditions where the pressure was 1.1×10$^{-2}$ Pa and the heating conditions were 400° C. for 4.5 hours and 408° C. for 3.0 hours. After the sublimation purification, 0.4 g of a target yellow solid was obtained in a collection rate of 48%.

The reaction scheme of the above synthesis method is illustrated in (b-1) below.

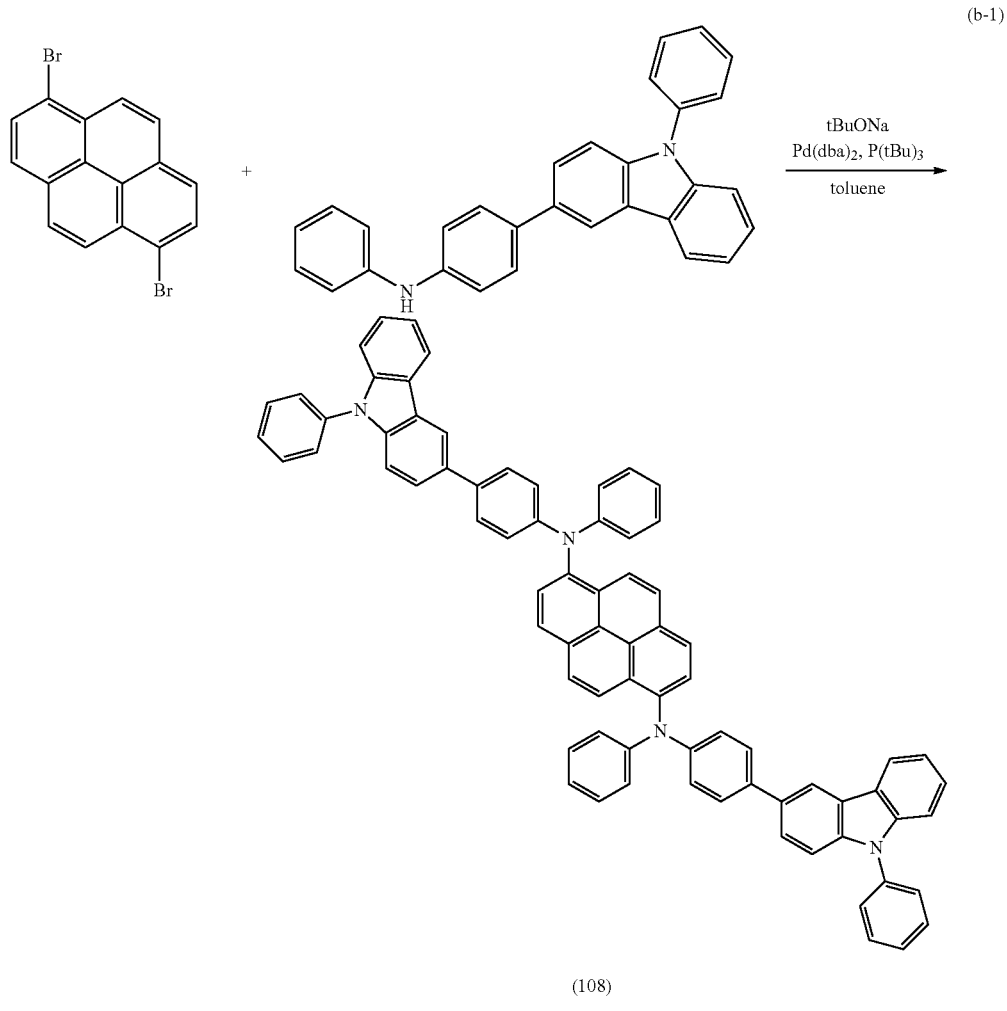

(b-1)

(108)

Figure 9A:
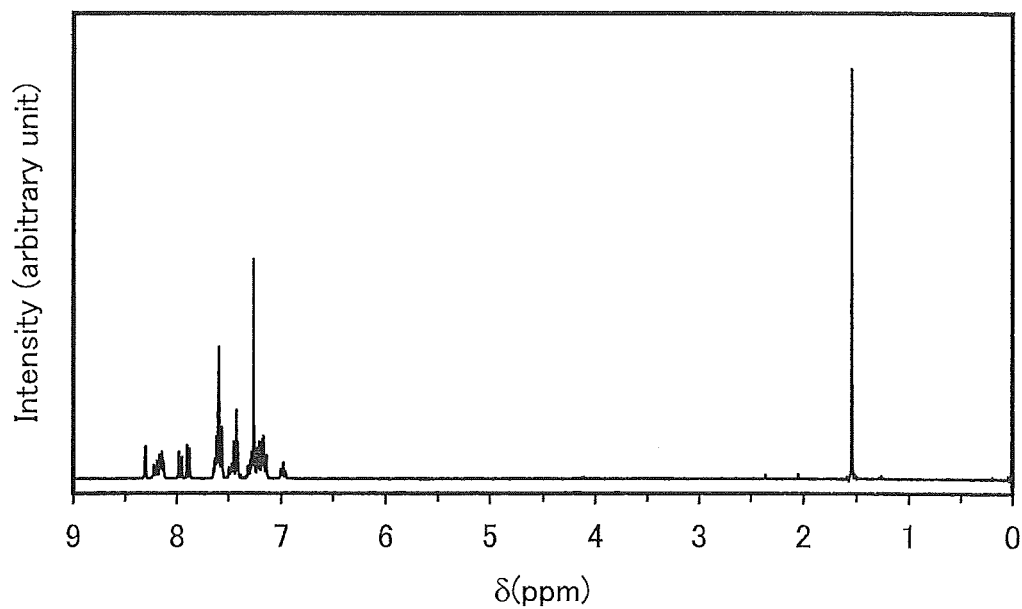
FIGS. 9A and 9B show $^1$H-NMR charts of a pyrene-based compound represented by a structural formula (108).
Figure 9B:
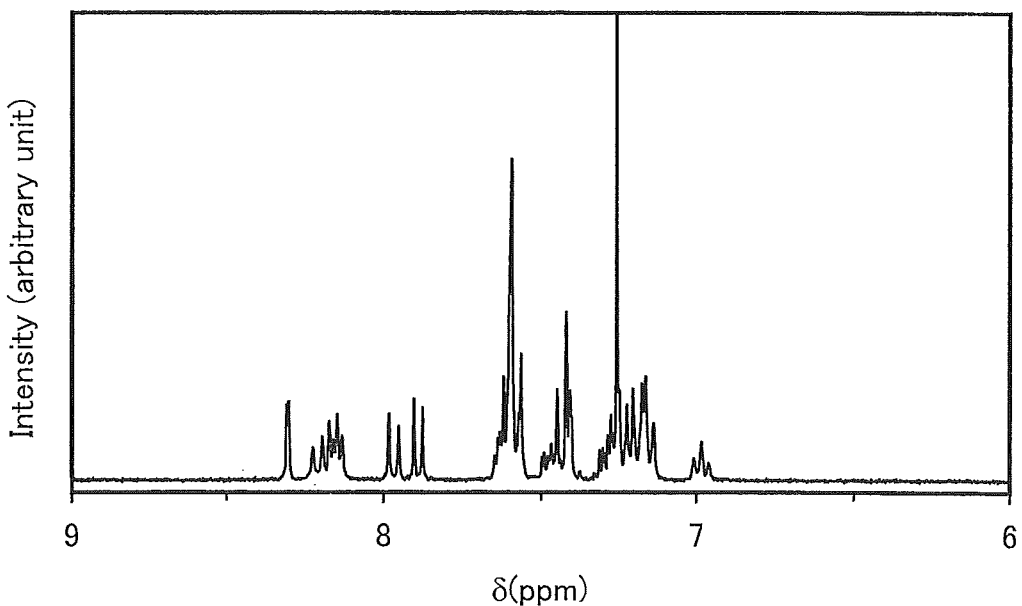

Results of nuclear magnetic resonance spectroscopy ($^1$H-NMR), by which the compound obtained by the above synthesis method was analyzed, are shown below. FIGS. 9A and 9B show the $^1$H-NMR charts. Note that FIG. 9B is an enlarged chart of FIG. 9A. The results reveal that N,N'-diphenyl-N,N'-(1,6-pyrenyl)-N,N'-bis[4-(9-phenyl-9H-carbazol-3-yl)phenyl]diamine (abbreviation: 1,6PCBAPrn), the pyrene-based compound which is one embodiment of the present invention and represented by the above structural formula (108), was obtained.

$^1$H NMR (CHCl$_3$, 300 MHz): δ=6.98 (t, J=7.2 Hz, 2H), 7.14-7.31 (m, 14H), 7.38-7.50 (m, 8H), 7.56-7.64 (m, 14H), 7.89 (d, J=7.8 Hz, 2H), 7.97 (d, J=9.3 Hz, 2H), 8.13-8.17 (m, 4H), 8.21 (d, J=9.3 Hz, 2H), 8.31 (d, J=2.1 Hz, 2H).

Next, ultraviolet-visible absorption spectra (hereinafter simply referred to as "absorption spectra") and emission spectra of 1,6PCBAPm (abbreviation) were measured. The absorption spectra were measured using an ultraviolet-visible light spectrophotometer (V550 type manufactured by JASCO Corporation). The emission spectra were measured using a fluorescence spectrophotometer (FS920 manufactured by Hamamatsu Photonics K.K.). The absorption spectra and the emission spectra of a toluene solution of 1,6PCBAPm (abbreviation) and a thin film of 1,6PCBAPm (abbreviation) were measured. Put in a quartz cell, the toluene solution was subjected to the measurement at room temperature. As for the thin film, the thin film which was deposited on a quartz substrate by evaporation was used. In order to obtain the absorption spectrum of the thin film, an absorption spectrum of quartz was subtracted from an absorption spectrum of the thin film and quartz.

Figure 10A:
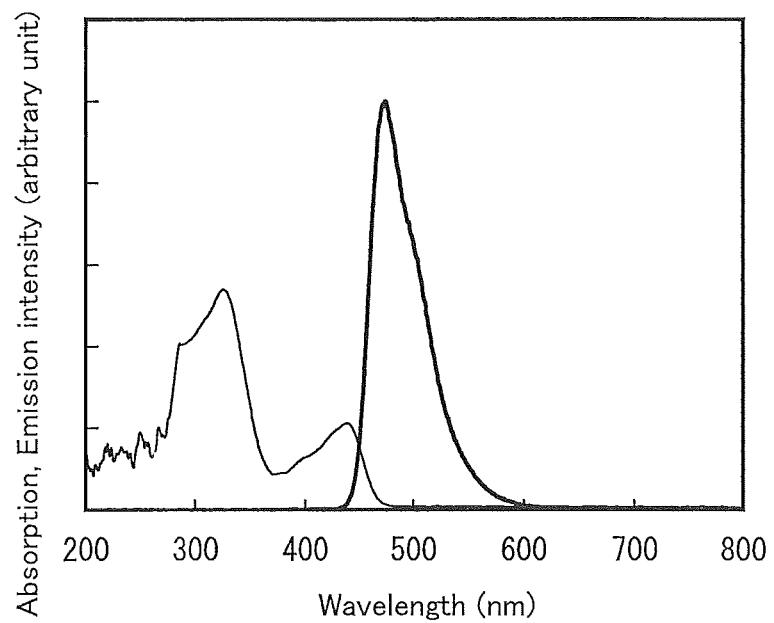
FIGS. 10A and 10B show ultraviolet-visible absorption spectra and emission spectra of the pyrene-based compound represented by the structural formula (108).
Figure 10B:
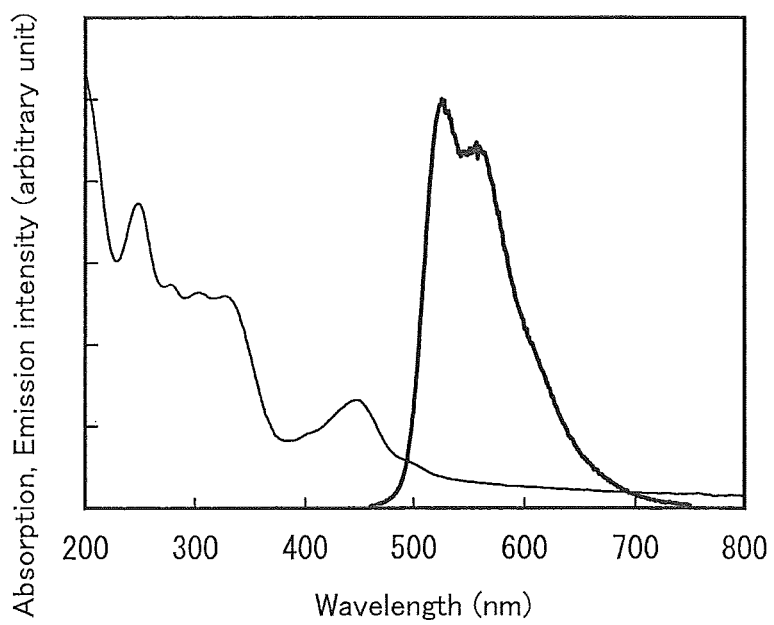

FIGS. 10A and 10B show measurement results of the absorption spectra and emission spectra. FIG. 10A shows the measurement results of the toluene solution of 1,6PCBAPrn (abbreviation). FIG. 10B shows the measurement results of the thin film of 1,6PCBAPrn (abbreviation). In each of FIGS. 10A and 10B, the horizontal axis represents wavelength (nm) and the vertical axis represents absorption intensity (arbitrary unit) or emission intensity (arbitrary unit). In each of FIGS. 10A and 10B, two solid lines are shown; a thin line represents the absorption spectrum, and a thick line represents the emission spectrum.

In the case of the toluene solution of 1,6PCBAPrn (abbreviation), an absorption peak is observed at around 439 nm as shown in FIG. 10A. In the case of the thin film of 1,6PCBAPrn (abbreviation), an absorption peak is observed at around 448 nm as shown in FIG. 10B.

Further, in the case of the toluene solution of 1,6PCBAPrn (abbreviation), the maximum emission wavelength is 474 nm (excitation wavelength: 370 nm) as shown in FIG. 10A. In the case of the thin film of 1,6PCBAPrn (abbreviation), the maximum emission wavelength is 526 nm (excitation wavelength: 438 nm) as shown in FIG. 10B.

As described above, 1,6PCBAPrn (abbreviation) was found to emit blue-green light with high color purity and accordingly can be used as a blue-green light-emitting material.

Further, the HOMO level and the LUMO level of 1,6PCBAPrn (abbreviation) were obtained by cyclic voltammetry (CV) measurement. An electrochemical analyzer (ALS model 600A or 600C, manufactured by BAS Inc.) was used for the CV measurement.

Further, as for the solution used for the CV measurement, dehydrated dimethylformamide (DMF, manufactured by Sigma-Aldrich Inc., 99.8%, Catalog No. 22705-6) was used as a solvent, and tetra-n-butylammonium perchlorate (n-Bu$_4$NClO$_4$, manufactured by Tokyo Chemical Industry Co., Ltd., Catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 2 mmol/L.

A platinum electrode (PTE platinum electrode, manufactured by BAS Inc.) was used as a working electrode, a platinum electrode (Pt counter electrode for VC-3 (5 cm), manufactured by BAS Inc.) was used as an auxiliary electrode, and an Ag/Ag$^+$ electrode (RE-7 reference electrode for nonaqueous solvent, manufactured by BAS Inc.) was used as a reference electrode. The CV measurement was performed under the following conditions: room temperature (20° C. to 25° C.) and a scan rate of 0.1 V/sec. Note that the potential energy of the reference electrode with respect to the vacuum level was assumed to be −4.94 eV in this example.

On the assumption that the intermediate potential (the half-wave potential) between the oxidation peak potential E$_{pa}$ and the reduction peak potential E$_{pe}$ which are obtained in the CV measurement corresponds to the HOMO level, the HOMO level of 1,6PCBAPrn (abbreviation) was calculated to be −5.19 eV, and the LUMO level of 1,6PCBAPrn (abbreviation) was calculated to be −2.62 eV.

Note that 1,6PCBAPrn (abbreviation) synthesized in this example and another pyrene-based compound having a different HOMO level but having substantially the same LUMO level are used to form a stack-type light-emitting layer. The stack-type light-emitting layer has a hole-trapping property at the interface between the stacked light-emitting layers but is unlikely to block electron transfer.

Example 3

Figure 11:
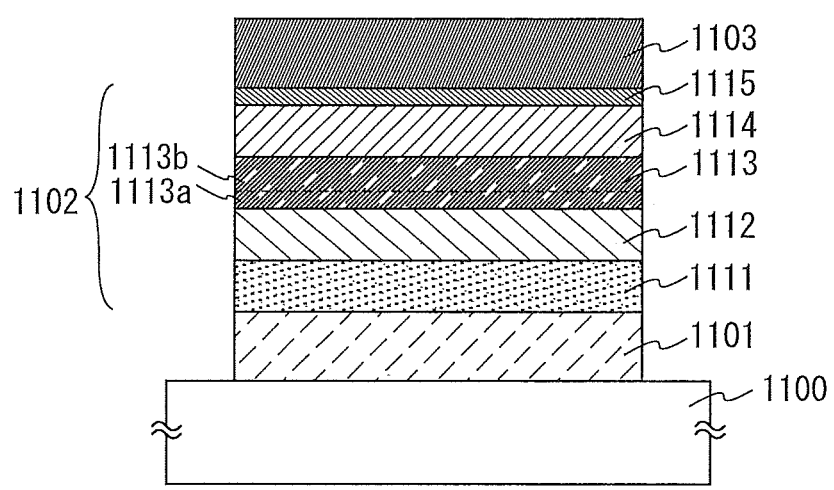
FIG. 11 illustrates a light-emitting element 1.

In this example, a light-emitting element 1 including a light-emitting layer formed using the pyrene-based compound N,N′-diphenyl-N,N′-(1,6-pyrenyl)-N,N′-bis(9-phenyl-9H-carbazol-3-yl)diamine (1,6PCAPm (abbreviation) (the structural formula (100)) will be described with reference to FIG. 11. Chemical formulae of materials used in this example are shown below.

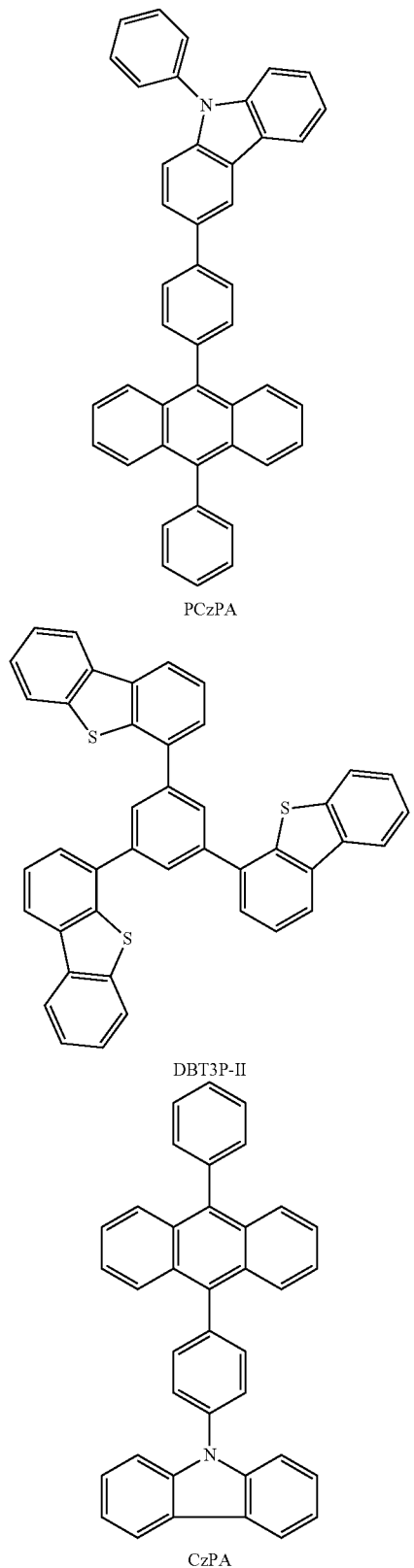

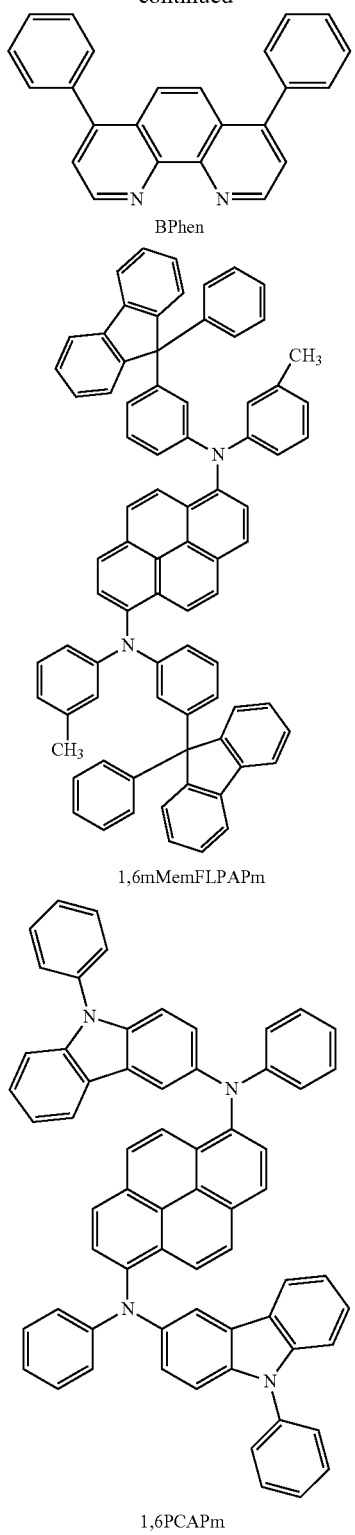

BPhen 1,6mMemFLPAPrn 1,6PCAPrn ((Fabrication of Light-emitting Element 1))

First, a film of indium tin oxide containing silicon oxide (ITSO) was formed over a glass substrate 1100 by a sputtering method, so that a first electrode 1101 functioning as an anode was formed. Note that the thickness was set to 110 nm and the electrode area was set to 2 mm×2 mm.

Next, as pretreatment for forming the light-emitting element 1 over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a substrate holder in the vacuum evaporation apparatus so that a surface on which the first electrode 1101 was provided faced downward. In this example, a case is described in which a hole-injection layer 1111, a hole-transport layer 1112, a light-emitting layer 1113, an electron-transport layer 1114, and an electron-injection layer 1115 which are included in an EL layer 1102 are sequentially formed.

The pressure in the vacuum evaporation apparatus was reduced to about $10^{-4}$ Pa. Then, 1,3,5-tri(dibenzothiophen-4-yl)benzene (abbreviation: DBT3P-II) and molybdenum (VI) oxide were co-evaporated with a mass ratio of DBT3P-II (abbreviation) to molybdenum oxide being 4:2, whereby the hole-injection layer 1111 was formed over the first electrode 1101. The thickness of the hole-injection layer 1111 was set to 70 nm. Note that a co-evaporation method is an evaporation method by which a plurality of different substances is concurrently vaporized from respective different evaporation sources.

Next, the hole-transport layer 1112 was formed by evaporation of 9-phenyl-3-[4-(10-phenyl-9-anthryl)phenyl]-9H-carbazole (abbreviation: PCzPA) to a thickness of 30 nm.

Next, the light-emitting layer 1113 was formed over the hole-transport layer 1112. Note that the light-emitting layer 1113 in this example has a structure in which two layers, a first light-emitting layer 1113a and a second light-emitting layer 1113b, are stacked. First, the first light-emitting layer 1113a was formed to a thickness of 5 nm by co-evaporation of 9-[4-(10-phenyl-9-anthryl)phenyl]-9H-carbazole (abbreviation: CzPA) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) with a mass ratio of CzPA (abbreviation) to 1,6mMemFLPAPrn (abbreviation) being 1:0.05. Then, the second light-emitting layer 1113b was formed to a thickness of 20 nm by co-evaporation of 9-[4-(10-phenyl-9-anthryl)phenyl]-9H-carbazole (abbreviation: CzPA) and N,N'-diphenyl-N,N'-(1,6-pyrenyl)-N,N'-bis(9-phenyl-9H-carbazol-3-yl)diamine (abbreviation: 1,6PCAPrn) with a mass ratio of CzPA (abbreviation) to 1,6PCAPrn (abbreviation) being 1:0.1. Thus, the light-emitting layer 1113 was formed.

Next, over the light-emitting layer 1113, the electron-transport layer 1114 was formed in such a manner that a film of 9-[4-(10-phenyl-9-anthryl)phenyl]-9H-carbazole (abbreviation: CzPA) was formed by evaporation to a thickness of 10 nm and then a film of bathophenanthroline (abbreviation: Bphen) was formed by evaporation to a thickness of 15 in. Further, over the electron-transport layer 1114, a film of lithium fluoride was formed by evaporation to a thickness of 1 nm to form the electron-injection layer 1115.

Lastly, over the electron-injection layer 1115, an aluminum film was formed by evaporation to a thickness of 200 nm as a second electrode 1103 functioning as a cathode. Thus, the light-emitting element 1 was fabricated. Note that, in all the above evaporation steps, evaporation was performed by a resistance-heating method.

Table 1 shows an element structure of the light-emitting element 1 obtained as described above.

TABLE 1

| | First electrode | Hole-injection layer | Hole-transport layer | Light-emitting layer | | Electron-transport layer | Electron-injection layer | Second electrode |
|---|---|---|---|---|---|---|---|---|
| Light-emitting element 1 | ITSO (110 nm) | DBT3P-II:MoOx (4:2, 70 nm) | PCzPA (30 nm) | CzPA:1, mMemFLPAPrn (1:0.05, 5 nm) | CzPA:1, 6mPCAPrn (1:0.1, 20 nm) | CzPA (10 nm) | Bphen (15 nm) | LiF (1 nm) | Al (200 nm) |

The fabricated light-emitting element 1 was sealed in a glove box containing a nitrogen atmosphere so as not to be exposed to air.

((Operation Characteristics of Light-Emitting Element 1))

Operation characteristics of the fabricated light-emitting element 1 were measured. Note that the measurements were carried out at room temperature (in an atmosphere kept at 25° C.).

Figure 12:
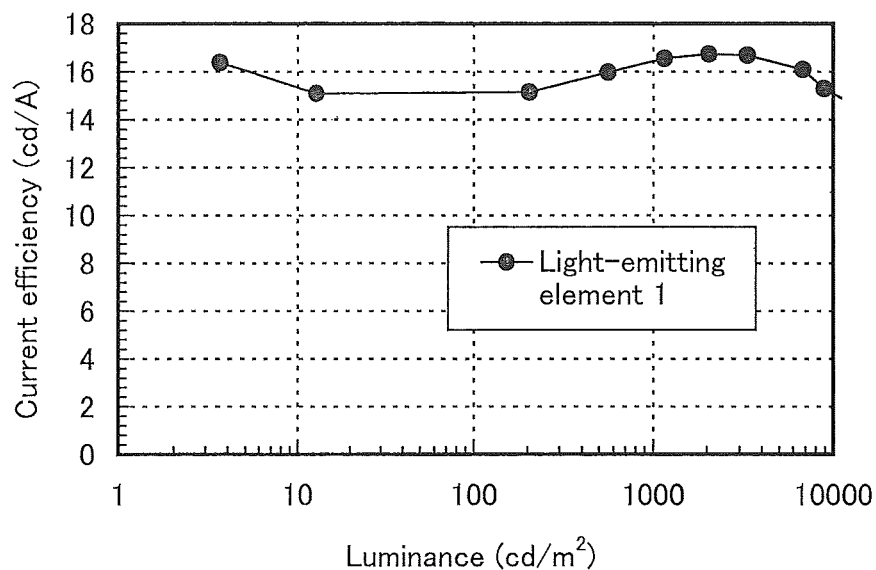
FIG. 12 shows luminance-current efficiency characteristics of the light-emitting element 1.
Figure 13:
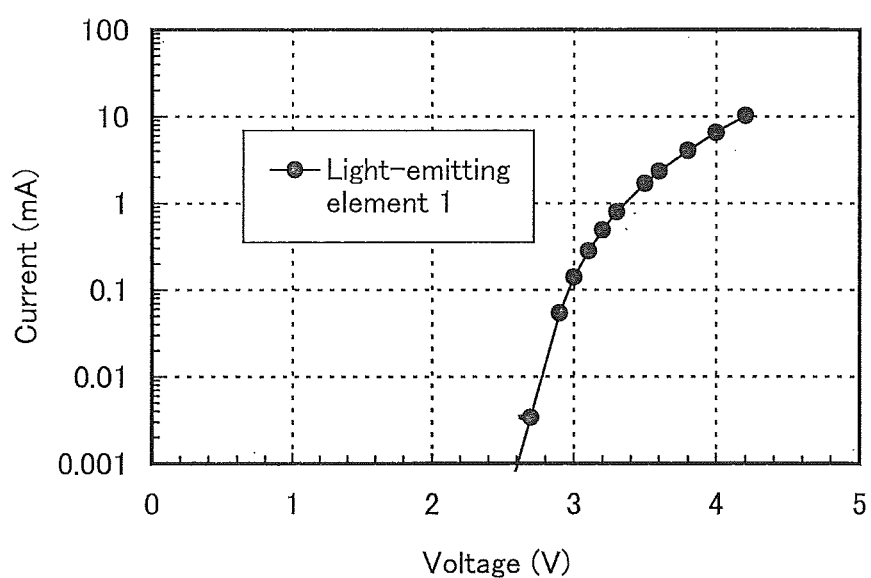
FIG. 13 shows voltage-current characteristics of the light-emitting element 1.
Figure 14:
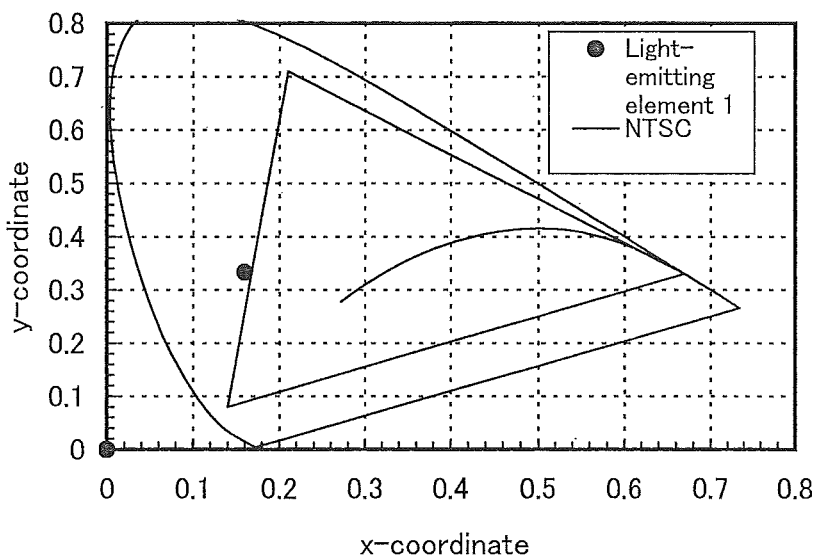
FIG. 14 is a chromaticity diagram showing the chromaticity of the light-emitting element 1.

FIG. 12 shows luminance-current efficiency characteristics of the light-emitting element 1. In FIG. 12, the vertical axis represents current efficiency (cd/A), and the horizontal axis represents luminance (cd/m$^2$). FIG. 13 shows voltage-current characteristics of the light-emitting element 1. Note that in FIG. 13, the vertical axis represents current (mA), and the horizontal axis represents voltage (V). FIG. 14 shows the CIE chromaticity coordinates of the light-emitting element 1. Note that in FIG. 14, the vertical axis represents the y-coordinate, and the horizontal axis represents the x-coordinate. Table 2 below shows initial values of main characteristics of the light-emitting element 1 at a luminance of about 1000 cd/m$^2$

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 1 | 3.1 | 0.28 | 7.0 | (0.16, 0.33) | 1200 | 17 | 17 | 8.5 |

The above results show that the light-emitting element 1 fabricated in this example has high external quantum efficiency, which means its high emission efficiency. Moreover, as for color purity, it can be found that the light-emitting element exhibits blue-green emission with excellent color purity.

Figure 15:
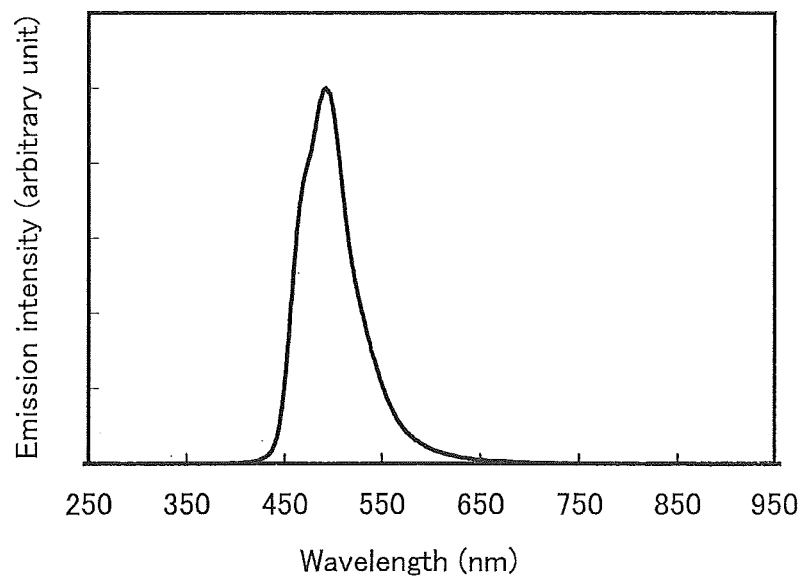
FIG. 15 shows an emission spectrum of the light-emitting element 1.

FIG. 15 shows an emission spectrum when a current at a current density of 25 mA/cm$^2$ was supplied to the light-emitting element 1. FIG. 15 shows that the emission spectrum of the light-emitting element 1 has peaks at around 491 nm and 470 nm, which indicates that the emission spectrum is derived from emission from the pyrene-based compounds 1,6PCAPrn (abbreviation) and 1,6mMemFLPAPrn (abbreviation).

Figure 16:
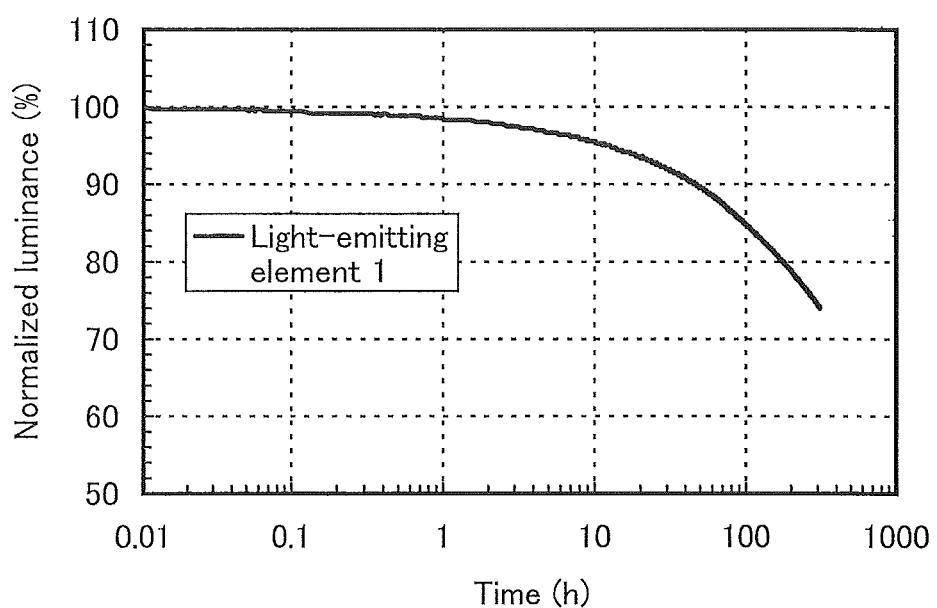
FIG. 16 shows reliability of the light-emitting element 1.

The light-emitting element 1 was subjected to a reliability test. The results are shown in FIG. 16. Note that in the reliability test, the light-emitting element 1 was driven under the conditions where the initial luminance was set to 5000 cd/m$^2$ and the current density was constant. As a result, the light-emitting element 1 kept about 74% of the initial luminance after 300 hours elapsed. Thus, the reliability test revealed high reliability of the light-emitting element 1.

The light-emitting element described in this example emits blue light originating from 1,6mMemFLPAPrn (abbreviation) and blue-green light originating from 1,6PCAPrn (abbreviation) which are guest materials contained in the light-emitting layer. In general, the external quantum efficiency (7.2%) of a light-emitting element which contains 1,6PCAPrn (abbreviation) as a guest material and emits blue-green light tends to be lower than the external quantum efficiency (8.4%) of a light-emitting element which contains 1,6mMemFLPAPrn (abbreviation) as a guest material and emits blue light. In the case of this example, even though containing both the substances as guest materials, the light-emitting element has an external quantum efficiency of 8.5% which is higher or substantially the same.

Therefore, as described in this example, a light-emitting element is formed which includes stacked light-emitting layers containing a common host material and different pyrene-based compounds having different HOMO levels but having substantially the same LUMO levels (1,6PCBAPrn (abbreviation) with a HOMO level of −5.32 eV and a LUMO level of −2.75 eV and 1,6mMemFLPAPrn (abbreviation) with a HOMO level of −5.50 eV and a LUMO level of −2.82 eV) as guest materials.

Accordingly, a stack-type light-emitting layer can be formed which has a hole-trapping property at the interface between the stacked light-emitting layers due to the difference between the HOMO levels of the guest materials, but is unlikely to block electron transfer because the guest materials have substantially the same LUMO levels. Thus, a light-emitting element having high emission efficiency can be obtained. The common host material is preferably a material containing anthracene, particularly, a material containing anthracene and having no amine skeleton, such as CzPA (with a HOMO level of −5.64 eV and a LUMO level of −2.71 eV) used in this example. Thus, the light-emitting element can also have long lifetime. Furthermore, when another light-emitting layer which emits light of a different color is additionally stacked in the light-emitting element having the above structure, the light-emitting element can have better color rendering properties.

Reference Example

In this reference example, a synthesis example of N,N'-bis(3-methylphenyl)-N,N'-bis[3-(9-phenyl-9H-fluoren-9-yl)phenyl]-pyrene-1,6-diamine (abbreviation: 1,6mMemFL-PAPrn) used in Example 3 and represented by the following structural formula will be described.

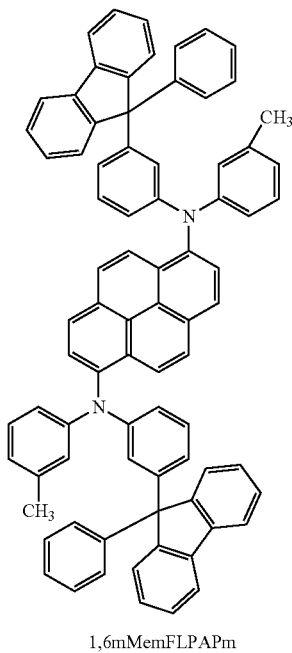 [SMILES: Cc1cccc(N(c2cccc(C3(c4ccccc4)c4ccccc4-c4ccccc43)c2)c2ccc3ccc4c(N(c5cccc(C)c5)c5cccc(C6(c7ccccc7)c7ccccc7-c7ccccc76)c5)ccc5ccc2c3c54)c1]

1,6mMemFLPAPm

Step 1: Method of Synthesizing 3-Methylphenyl-3-(9-phenyl-9H-fluoren-9-yl)phenylamine (abbreviation: mMemFLPA)

In a 200 mL three-neck flask were placed 3.2 g (8.1 mmol) of 9-(3-bromophenyl)-9-phenylfluorene and 2.3 g (24.1 mmol) of sodium tert-butoxide. The air in the flask was replaced with nitrogen. To this mixture were added 40.0 mL of toluene, 0.9 mL (8.3 mmol) of m-toluidine, and 0.2 mL of a 10% hexane solution of tri(tert-butyl)phosphine. The temperature of this mixture was set to 60° C., 44.5 mg (0.1 mmol) of bis(dibenzylideneacetone)palladium(0) was added to the mixture, and the temperature of this mixture was set to 80° C., followed by stirring for 2.0 hours. After the stirring, the mixture was subjected to suction filtration through Florisil, Celite, and alumina to give a filtrate. The obtained filtrate was concentrated to give a solid, which was then purified by silica gel column chromatography (the developing solvent has a 1:1 ratio of hexane to toluene) and recrystallized from a mixed solvent of toluene and hexane. Accordingly, 2.8 g of a target white solid was obtained in a yield of 82%. The synthesis scheme of Step 1 is illustrated in (C-1) below.

(C-1)

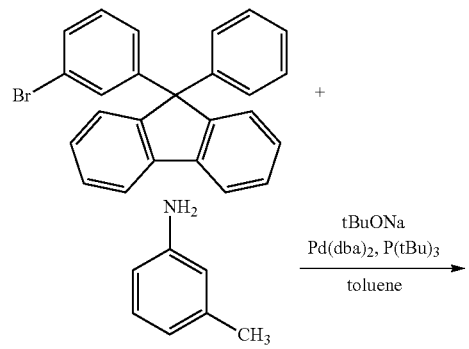

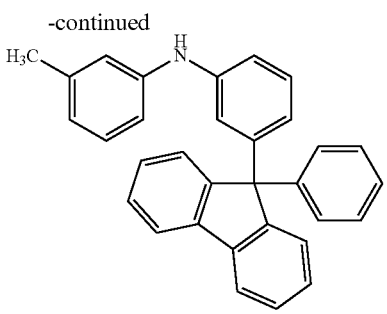

Step 2: Method of Synthesizing N,N'-Bis(3-methylphenyl)-N,N'-bis[3-(9-phenyl-9H-fluoren-9-yl)phenyl]-pyrene-1,6-di amine (abbreviation: 1,6mMem-FLPAPm)

In a 100 mL three-neck flask were placed 0.6 g (1.7 mmol) of 1,6-dibromopyrene, 1.4 g (3.4 mmol) of 3-methylphenyl-3-(9-phenyl-9H-fluoren-9-yl)phenylamine, and 0.5 g (5.1 mmol) of sodium tert-butoxide. The air in the flask was replaced with nitrogen. Then, 21.0 mL of toluene and 0.2 mL of a 10% hexane solution of tri(tert-butyl)phosphine were added to this mixture. The temperature of this mixture was set to 60° C., 34.9 mg (0.1 mmol) of bis(dibenzylideneacetone)palladium(0) was added to the mixture, and the temperature of this mixture was set to 80° C., followed by stirring for 3.0 hours. After the stirring, 400 mL of toluene was added to the mixture, and the mixture was heated. While the mixture was kept hot, it was subjected to suction filtration through Florisil, Celite, and alumina to give a filtrate. The filtrate was concentrated to give a solid, which was then purified by silica gel column chromatography (the developing solvent has a 3:2 ratio of hexane to toluene) to give a yellow solid. The obtained yellow solid was recrystallized from a mixed solvent of toluene and hexane to give 1.2 g of a target yellow solid in a yield of 67%.

By a train sublimation method, 1.0 g of the obtained yellow solid was purified. The sublimation purification was conducted under the conditions where the pressure was 2.2 Pa, the flow rate of an argon gas was 5.0 mL/min, and the yellow solid was heated at 317° C. After the sublimation purification, 1.0 g of a target yellow solid was obtained in a collection rate of 93%. The synthesis scheme of Step 2 is illustrated in (C-2) below.

(C-2)

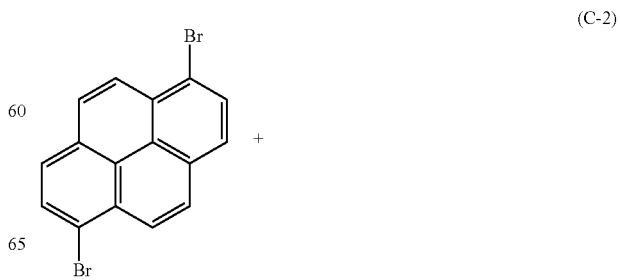

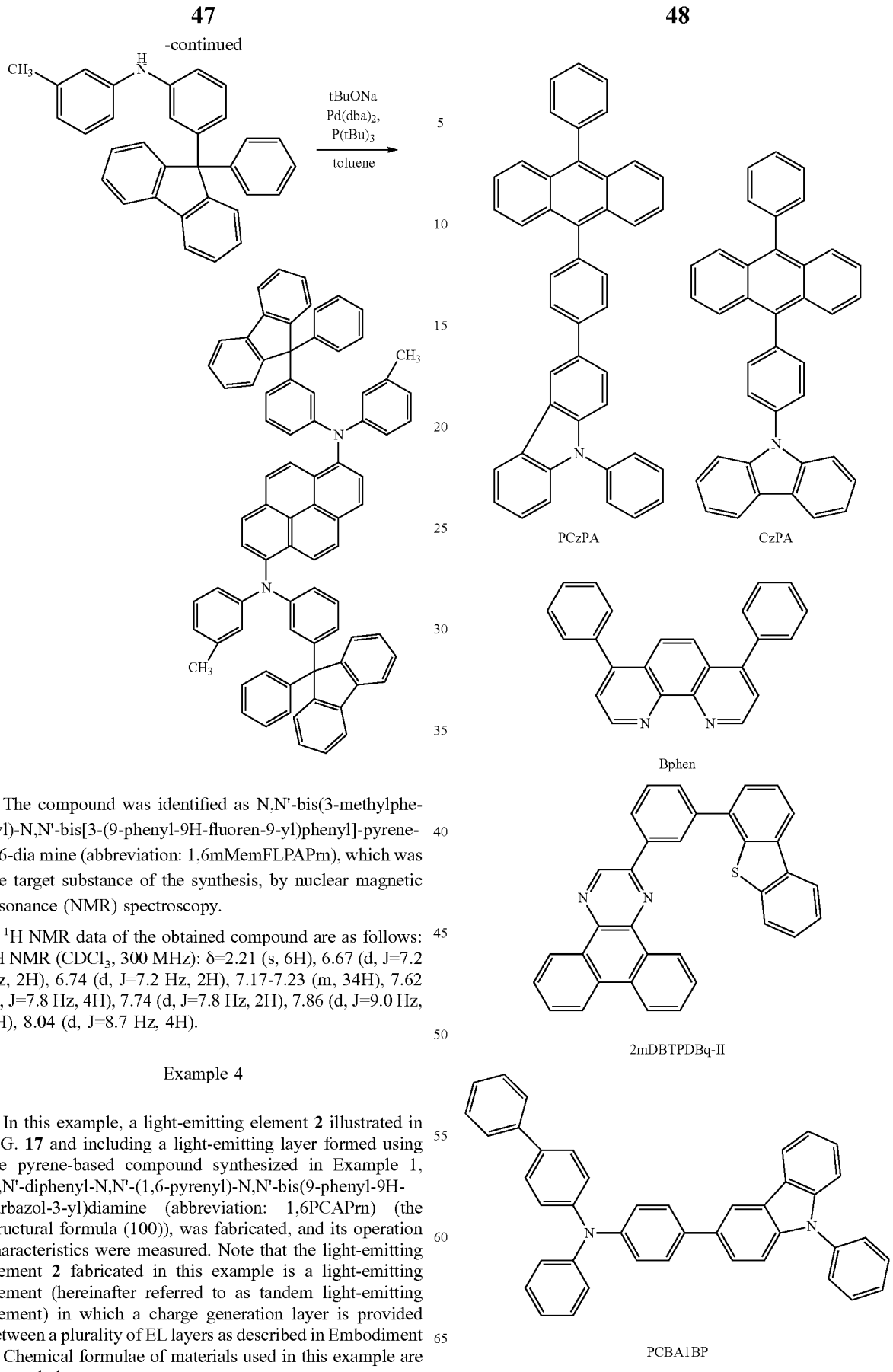

The compound was identified as N,N'-bis(3-methylphenyl)-N,N'-bis[3-(9-phenyl-9H-fluoren-9-yl)phenyl]-pyrene-1,6-diamine (abbreviation: 1,6mMemFLPAPrn), which was the target substance of the synthesis, by nuclear magnetic resonance (NMR) spectroscopy.

$^1$H NMR data of the obtained compound are as follows: $^1$H NMR (CDCl$_3$, 300 MHz): δ=2.21 (s, 6H), 6.67 (d, J=7.2 Hz, 2H), 6.74 (d, J=7.2 Hz, 2H), 7.17-7.23 (m, 34H), 7.62 (d, J=7.8 Hz, 4H), 7.74 (d, J=7.8 Hz, 2H), 7.86 (d, J=9.0 Hz, 2H), 8.04 (d, J=8.7 Hz, 4H).

Example 4

Figure 17:
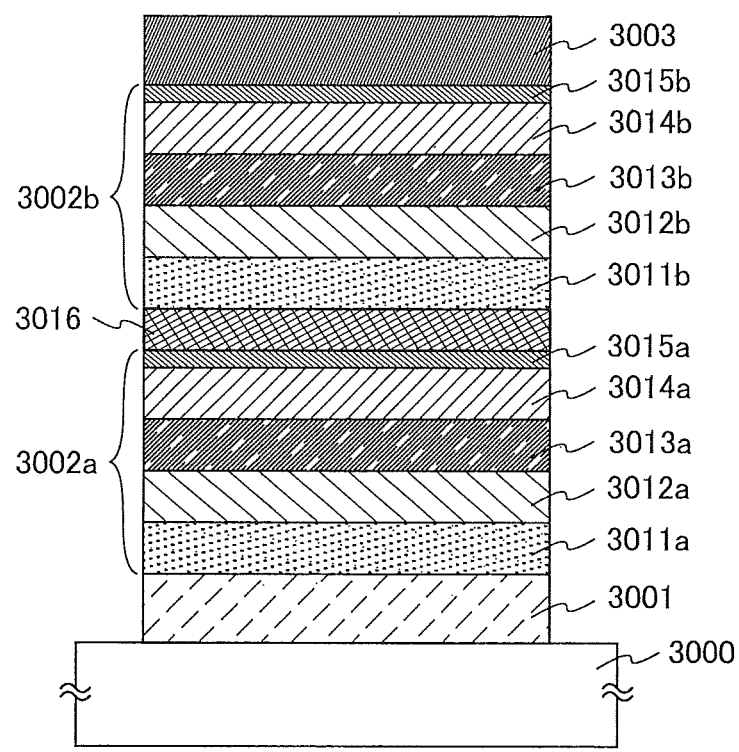
FIG. 17 illustrates a light-emitting element 2.

In this example, a light-emitting element 2 illustrated in FIG. 17 and including a light-emitting layer formed using the pyrene-based compound synthesized in Example 1, N,N'-diphenyl-N,N'-(1,6-pyrenyl)-N,N'-bis(9-phenyl-9H-carbazol-3-yl)diamine (abbreviation: 1,6PCAPrn) (the structural formula (100)), was fabricated, and its operation characteristics were measured. Note that the light-emitting element 2 fabricated in this example is a light-emitting element (hereinafter referred to as tandem light-emitting element) in which a charge generation layer is provided between a plurality of EL layers as described in Embodiment 3. Chemical formulae of materials used in this example are shown below.

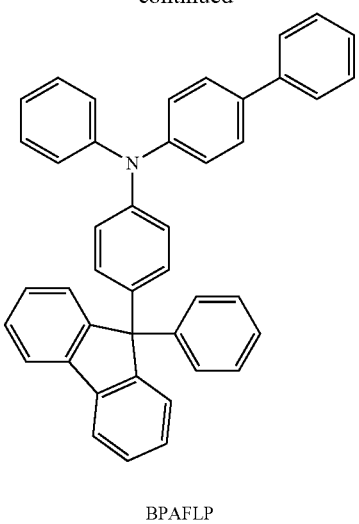

BPAFLP

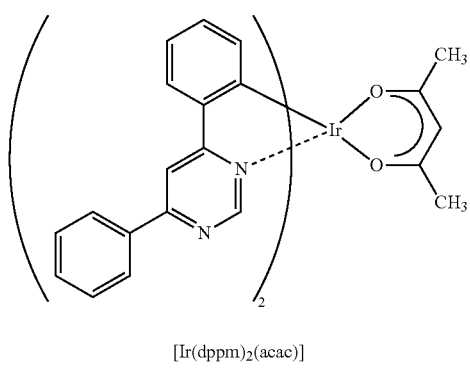

[Ir(dppm)₂(acac)]

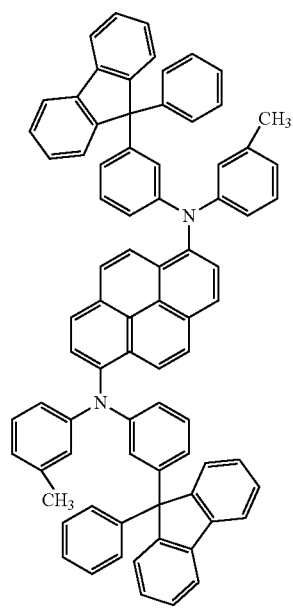

1,6mMemFLPAPrn

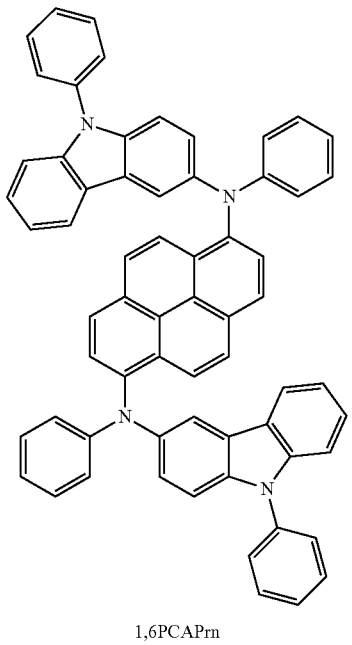

(100)

1,6PCAPrn ((Fabrication of Light-emitting Element 2))

First, a film of indium tin oxide containing silicon oxide (ITSO) was formed over a glass substrate 3000 by a sputtering method, so that a first electrode 3001 functioning as an anode was formed. Note that the thickness was set to 110 nm and the electrode area was set to 2 mm×2 mm.

Next, as pretreatment for forming the light-emitting element 2 over the substrate 3000, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 3000 was cooled down for about 30 minutes.

Next, the substrate 3000 was fixed to a substrate holder in the vacuum evaporation apparatus so that a surface on which the first electrode 3001 was provided faced downward. In this example, a case is described in which a first hole-injection layer 3011a, a first hole-transport layer 3012a, a first light-emitting layer 3013a, a first electron-transport layer 3014a, and a first electron-injection layer 3015a which are included in a first EL layer 3002a are sequentially formed, a charge generation layer 3016 is formed, and then a second hole-injection layer 3011b, a second hole-transport layer 3012b, a second light-emitting layer 3013b, a second electron-transport layer 3014b, and a second electron-injection layer 3015b which are included in a second EL layer 3002b are formed.

The pressure in the vacuum evaporation apparatus was reduced to about $10^{-4}$ Pa. Then, 9-[4-(9-phenylcarbazol-3-yl)]phenyl-10-phenylanthracene (abbreviation: PCzPA) and molybdenum(VI) oxide were co-evaporated with a mass ratio of PCzPA (abbreviation) to molybdenum oxide being 1:0.5, whereby the first hole-injection layer 3011a was formed over the first electrode 3001. The thickness of the first hole-injection layer 3011a was set to 33.3 nm. Note that a co-evaporation method is an evaporation method by which a plurality of different substances is concurrently vaporized from respective different evaporation sources.

Next, the first hole-transport layer 3012a was formed by evaporation of PCzPA (abbreviation) to a thickness of 30 nm.

Next, the first light-emitting layer 3013a was formed over the first hole-transport layer 3012a. A film was formed to a thickness of 5 nm by co-evaporation of 9-[4-(10-phenyl-9-anthracenyl)phenyl]-9H-carbazole (abbreviation: CzPA) and N,N'-bis(3-methylphenyl)-N,N'-bis[3-(9-phenyl-9H-fluoren-9-yl)phenyl]-pyrene-1, 6-diamine (abbreviation: 1,6mMemFLPAPrn) with a mass ratio of CzPA (abbreviation) to 1,6mMemFLPAPm (abbreviation) being 1:0.05. Then, a film was formed thereover to a thickness of 25 nm by co-evaporation of CzPA (abbreviation) and N,N'-diphenyl-N,N'-(1,6-pyrenyl)-N,N'-bis(9-phenyl-9H-carbazol-3-yl)diamine (abbreviation: 1,6PCAPrn) with a mass ratio of CzPA (abbreviation) to 1,6PCAPrn (abbreviation) being 1:0.01. Thus, the first light-emitting layer 3013a was formed.

Next, over the first light-emitting layer 3013a, the first electron-transport layer 3014a was formed in such a manner that a film of CzPA (abbreviation) was formed by evaporation to a thickness of 5 nm and then a film of bathophenanthroline (abbreviation: Bphen) was formed by evaporation to a thickness of 15 nm. Further, over the first electron-transport layer 3014a, a film of lithium oxide ($Li_2O$) was formed by evaporation to a thickness of 0.1 nm to form the first electron-injection layer 3015a.

Then, copper phthalocyanine (abbreviation: CuPc) was evaporated to a thickness of 2 nm over the first electron-injection layer 3015a, whereby the charge generation layer 3016 was formed.

Then, PCzPA (abbreviation) and molybdenum(VI) oxide were co-evaporated with a mass ratio of PCzPA (abbreviation) to molybdenum oxide being 1:0.5, whereby the second hole-injection layer 3011b was formed over the charge generation layer 3016. The thickness of the second hole-injection layer 3011b was set to 50 nm.

Next, the second hole-transport layer 3012b was formed by evaporation of 4-phenyl-4'-(9-phenylfluoren-9-yl)triphenylamine (abbreviation: BPAFLP) to a thickness of 20 nm.

Next, the second light-emitting layer 3013b was formed over the second hole-transport layer 3012b. The second light-emitting layer 3013b was formed by co-evaporation of 2-[3-(dibenzothiophen-4-yl)phenyl]dibenzo[f,h]quinoxaline (abbreviation: 2mDBTPDBq-II), 4-phenyl-4'-(9-phenyl-9H-carbazol-3-yl)triphenylamine (abbreviation: PCBA1BP), and (acetylacetonato)bis(4,6-diphenylpyrimidinato)iridium (III) (abbreviation: [Ir(dppm)$_2$(acac)]) with a mass ratio of 2mDBTPDBq-II (abbreviation) to PCBA1BP (abbreviation) and [Ir(dppm)$_2$(acac)](abbreviation) being 0.8:0.2:0.06. The thickness of the second light-emitting layer 3013b was set to 40 nm.

Next, over the second light-emitting layer 3013b, the second electron-transport layer 3014b was formed in such a manner that a film of 2mDBTPDBq-II (abbreviation) was formed by evaporation to a thickness of 15 nm and then a film of Bphen (abbreviation) was formed by evaporation to a thickness of 15 nm. Further, over the second electron-transport layer 3014b, a film of lithium fluoride (LiF) was formed by evaporation to a thickness of 0.1 nm, whereby the second electron-injection layer 3015b was formed.

Lastly, over the second electron-injection layer 3015b, an aluminum film was formed by evaporation to a thickness of 200 nm as a second electrode 3003 functioning as a cathode. Thus, the light-emitting element 2 was fabricated. Note that, in all the above evaporation steps, evaporation was performed by a resistance-heating method.

Table 3 shows an element structure of the light-emitting element 2 obtained as described above.

TABLE 3

| | First electrode | First hole-injection layer | First hole-transport layer | First light-emitting layer | First eletron-transport layer | First electron-injection layer | Charge generation layer |
|---|---|---|---|---|---|---|---|
| Light-emitting element 2 | ITSO (110 nm) | PCzPA:MoOx (1:0.5, 33.3 nm) | PczPA (30 nm) | * | CzPA (5 nm) | Bphen (15 nm) | $Li_2O$ (0.1 nm) | CuPc (2 nm) |

| | Second hole-injection layer | Second hole-transport layer | Second light-emitting layer | Second electron-transport layer | Second electron-injection layer | Second electrode |
|---|---|---|---|---|---|---|
| Light-emitting element 2 | PCzPA:MoOx (1:0.5, 50 nm) | BPAFLP (20 nm) | ** | 2mDBTPDBq-II (15 nm) | Bphen (15 nm) | LiF (1 nm) | Al (200 nm) |

* CzPA:1,6mMemFLPAPrn (1:0.05, 5 nm)\CzPA:1,6PCAPrn (1:0.01, 25 nm)
** 2mDBTPDBq-II:PCBA1BP:[Ir(dppm)$_2$(acac)] (0.8:0.2:0.06, 40 nm)

The fabricated light-emitting element 2 was sealed in a glove box containing a nitrogen atmosphere so as not to be exposed to air (specifically, a sealant was applied to an outer edge of the element and heat treatment was performed at 80° C. for 1 hour at the time of sealing).

((Operation Characteristics of Light-Emitting Element 2))

Operation characteristics of the fabricated light-emitting element 2 were measured. Note that the measurements were carried out at room temperature (in an atmosphere kept at 25° C.).

Figure 18:
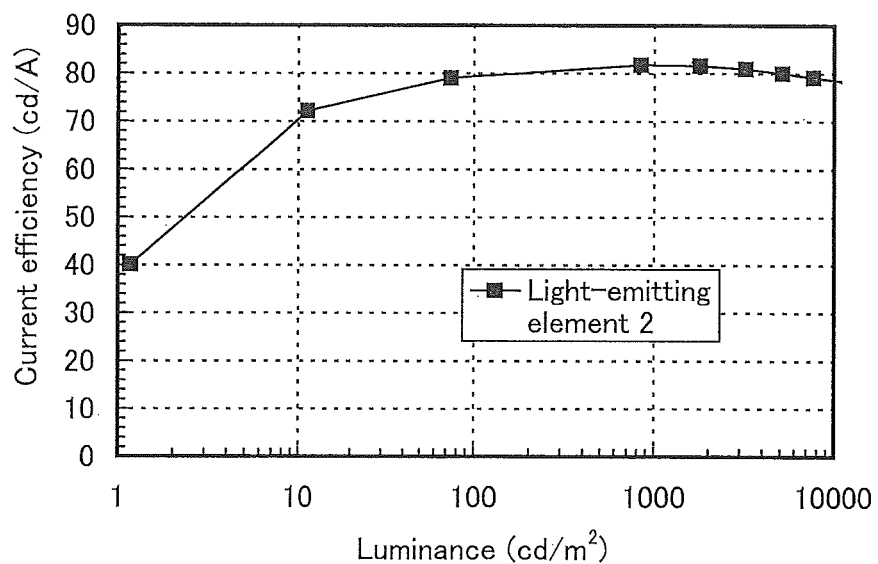
FIG. 18 shows luminance-current efficiency characteristics of the light-emitting element 2.
Figure 19:
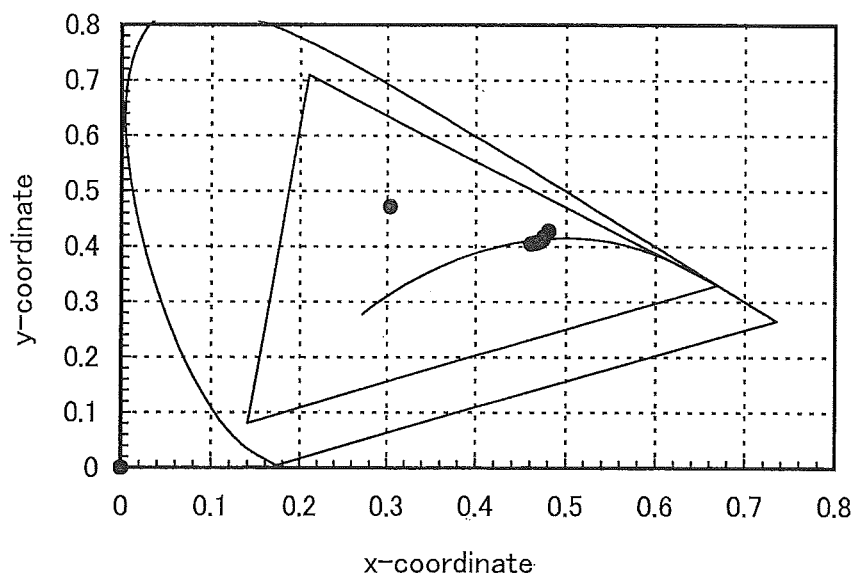
FIG. 19 is a chromaticity diagram showing the chromaticity of the light-emitting element 2.

FIG. 18 shows luminance-current efficiency characteristics of the light-emitting element 2. Note that in FIG. 18, the vertical axis represents current efficiency (cd/A), and the horizontal axis represents luminance (cd/m$^2$). FIG. 19 shows the CIE chromaticity coordinates of the light-emitting element 2. Note that in FIG. 19, the vertical axis represents the y-coordinate, and the horizontal axis represents the x-coordinate. Table 4 below shows initial values of main characteristics of the light-emitting element 2 at a luminance of about 1000 cd/m$^2$.

TABLE 4

|  | Voltage (V) | Current (mA) | Current density (mA/cm$^2$) | Chromaticity (x, y) | Luminance (cd/m$^2$) | Power efficiency (lm/W) | External quantum efficiency (%) |
|---|---|---|---|---|---|---|---|
| Light-emitting element 2 | 5.6 | 0.041 | 1.03 | (0.47, 0.41) | 840 | 46 | 31 |

The above results show that the light-emitting element 2 fabricated in this example has high external quantum efficiency, which means its high emission efficiency. Moreover, the chromaticity (x, y) shows that the light-emitting element 2 emits white light (incandescent color).

Figure 20:
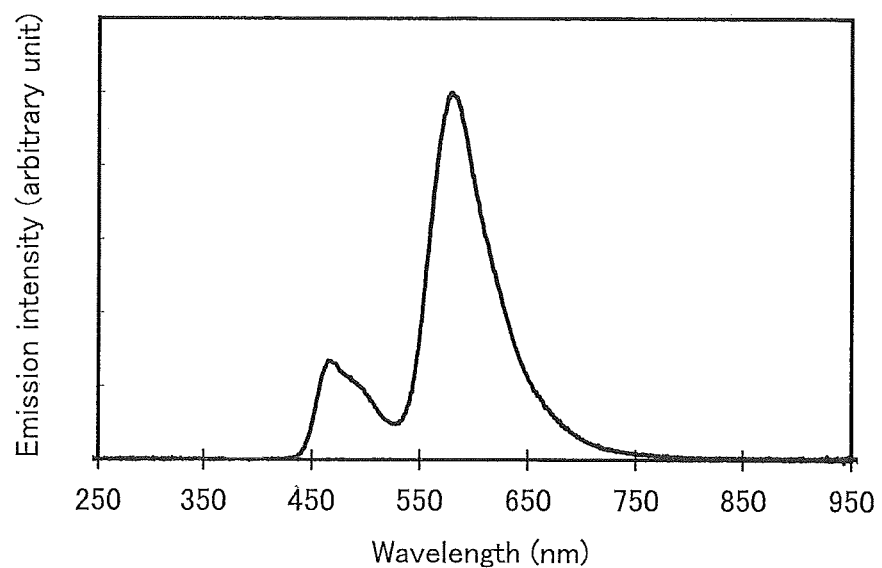
FIG. 20 shows an emission spectrum of the light-emitting element 2.

FIG. 20 shows an emission spectrum when a current at a current density of 0.1 mA/cm$^2$ was supplied to the light-emitting element 2. FIG. 20 shows that the emission spectrum of the light-emitting element 2 has peaks at around 471 nm and 581 nm, which indicates that the emission spectrum is derived from emission from the pyrene-based compounds 1,6PCAPrn (abbreviation) and 1,6mMemFLPAPrn (abbreviation) and the phosphorescent organometallic iridium complex [Ir(dppm)$_2$(acac)](abbreviation) contained in the light-emitting layers. Note that a general color rendering index (Ra) which is calculated from this spectrum is 43.6, which means good color rendering properties.

Therefore, as described in this example, a light-emitting element is formed which includes stacked light-emitting layers containing a common host material and different pyrene-based compounds having different HOMO levels but having substantially the same LUMO levels as guest materials. Accordingly, a stack-type light-emitting layer can be formed which has a hole-trapping property at the interface between the stacked light-emitting layers due to the difference between the HOMO levels of the guest materials, but is unlikely to block electron transfer because the guest materials have substantially the same LUMO levels. Thus, a light-emitting element having high emission efficiency can be obtained. Furthermore, in the light-emitting element described in this example, the light-emitting layer containing the phosphorescent organometallic iridium complex and emitting light of a different color is stacked. Thus, a white light-emitting element having still higher emission efficiency can be obtained.

This application is based on Japanese Patent Application serial no. 2011-223634 filed with Japan Patent Office on Oct. 11, 2011, the entire contents of which are hereby incorporated by reference.

What is claimed is:

1. A light-emitting element comprising a light-emitting layer between a pair of electrodes,
    wherein the light-emitting layer comprises a bipolar material as a host material and at least two kinds of pyrene-based compounds having different HOMO levels but having substantially the same LUMO levels as guest materials.

2. The light-emitting element according to claim 1, wherein the LUMO levels of the at least two kinds of pyrene-based compounds are within a range of ±0.1 eV.

3. The light-emitting element according to claim 1, wherein the bipolar material is a material comprising condensed aromatic hydrocarbon.

4. The light-emitting element according to claim 1, wherein the bipolar material comprises anthracene, pyrene, phenanthrene, triphenylene, or fluoranthene.

5. A light-emitting device comprising the light-emitting element according to claim 1.

6. An electronic device comprising the light-emitting device according to claim 5.

7. A lighting device comprising the light-emitting device according to claim 5.

8. A light-emitting element comprising a light-emitting layer between a pair of electrodes,
    wherein the light-emitting layer comprises a first light-emitting layer comprising a bipolar material and a first pyrene-based compound and a second light-emitting layer comprising the bipolar material and a second pyrene-based compound, and
    wherein the first pyrene-based compound and the second pyrene-based compound have different HOMO levels but have substantially the same LUMO levels.

9. The light-emitting element according to claim 8, wherein the LUMO levels of the first pyrene-based compound and the second pyrene-based compound are within a range of ±0.1 eV.

10. The light-emitting element according to claim 8, wherein the bipolar material is a material comprising condensed aromatic hydrocarbon.

11. The light-emitting element according to claim 8, wherein the bipolar material comprises anthracene, pyrene, phenanthrene, triphenylene, or fluoranthene.

12. A light-emitting device comprising the light-emitting element according to claim 8.

13. An electronic device comprising the light-emitting device according to claim 12.

14. A lighting device comprising the light-emitting device according to claim 12.

* * * * *